United States Patent
Sasamoto

(10) Patent No.: US 8,773,765 B2
(45) Date of Patent: Jul. 8, 2014

(54) ENDOSCOPE APPARATUS

(71) Applicant: Olympus Medical Systems Corp., Tokyo (JP)

(72) Inventor: Tsutomu Sasamoto, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/764,140

(22) Filed: Feb. 11, 2013

(65) Prior Publication Data

US 2013/0217965 A1 Aug. 22, 2013

Related U.S. Application Data

(63) Continuation of application No. PCT/JP2012/066353, filed on Jun. 27, 2012.

(30) Foreign Application Priority Data

Aug. 10, 2011 (JP) ................................. 2011-175313

(51) Int. Cl.
*A61B 1/05* (2006.01)
*A61B 1/00* (2006.01)

(52) U.S. Cl.
CPC ......... *A61B 1/00188* (2013.01); *A61B 1/00174* (2013.01); *A61B 1/051* (2013.01); *A61B 1/00096* (2013.01)
USPC ........... 359/684; 359/656; 359/649; 600/167; 600/118; 600/109

(58) Field of Classification Search
CPC ........... A61B 1/00188; A61B 1/00174; A61B 1/051; A61B 1/00096
USPC .......... 359/656–661, 684, 649; 600/167, 118, 600/109
See application file for complete search history.

(56) References Cited

U.S. PATENT DOCUMENTS 6,905,462 B1 * 6/2005 Homma et al. ............... 600/176
7,466,490 B2 * 12/2008 Igarashi ........................ 359/651

(Continued)

FOREIGN PATENT DOCUMENTS

| EP | 1 757 220 | 2/2007 |
|---|---|---|
| JP | 11-305115 | 11/1999 |
| JP | 2002-253489 | 9/2002 |
| JP | 2002-258166 | 9/2002 |

(Continued)

OTHER PUBLICATIONS

International Search Report, issued in corresponding International Application No. PCT/JP2012/066353.

*Primary Examiner* — Zachary Wilkes
(74) *Attorney, Agent, or Firm* — Kenyon & Kenyon LLP

(57) ABSTRACT

An endoscope apparatus includes an objective optical system mounted at a distal end portion of an endoscope, which is inserted into a tube cavity, and configured to form an image of an object in the tube cavity, the objective optical system including a focusing lens movable in an optical axis direction, a solid-state image pickup device for color image pickup configured to pick up the image formed by the objective optical system, a color separation filter being arranged for each pixel in the solid-state image pickup device, a focus adjusting mechanism configured to move the focusing lens and automatically adjust the objective optical system to a focus position in a focused state, a moving range switching section configured to perform switching of a moving range of the focusing lens, a moving range limiting section configured to limit the moving range in association with the switching by the moving range switching section, and the like.

16 Claims, 19 Drawing Sheets

(56) References Cited

U.S. PATENT DOCUMENTS

| | | | |
|---|---|---|---|
| 7,486,446 B2 * | 2/2009 | Mihara | 359/680 |
| 7,505,802 B2 * | 3/2009 | Yoshino | 359/708 |
| 2002/0055669 A1 * | 5/2002 | Konno | 600/167 |
| 2004/0130651 A1 | 7/2004 | Wakashiro | |
| 2006/0203361 A1 | 9/2006 | Kato | |
| 2007/0055100 A1 | 3/2007 | Kato et al. | |

FOREIGN PATENT DOCUMENTS

| | | |
|---|---|---|
| JP | 2004-205982 | 7/2004 |
| JP | 2005-323874 | 11/2005 |
| JP | 2006-251272 | 9/2006 |
| JP | 2009-066222 | 4/2009 |
| JP | 2011-048086 | 3/2011 |
| WO | 2005/110201 | 11/2005 |

* cited by examiner

FIG.2
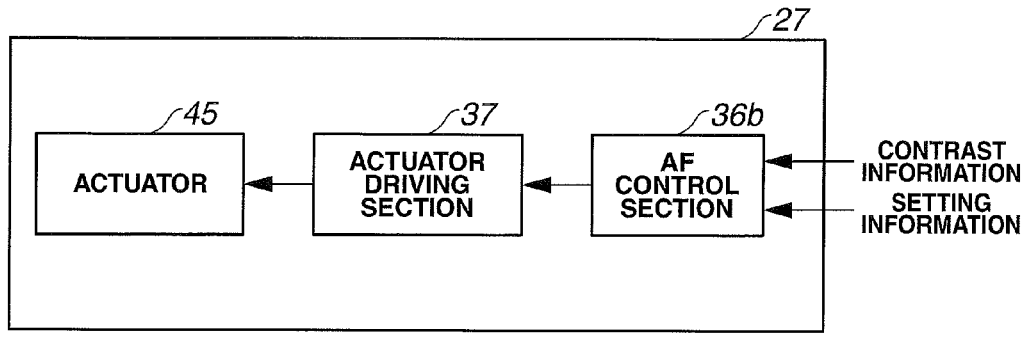
FIG.3A
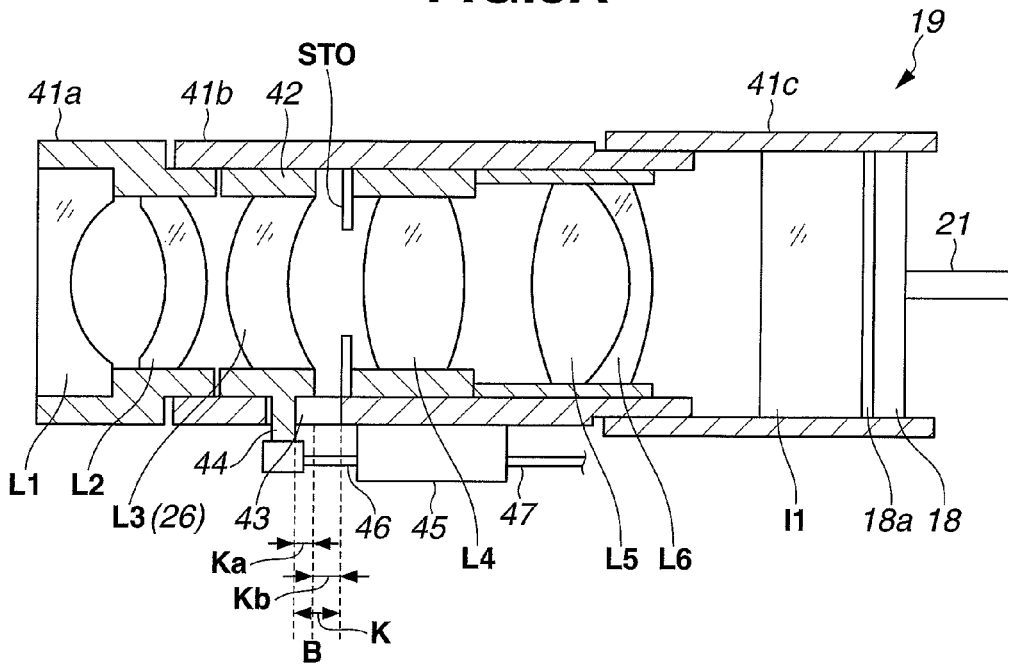
FIG.3B
| MOVING RANGE K | | | |
|---|---|---|---|
| FIRST MOVING RANGE Ka | | SECOND MOVING RANGE Kb | |
| CURRENT VALUE Ia | CURRENT VALUE Ib | CURRENT VALUE Ic | CURRENT VALUE Id |
| OBJECTIVE OPTICAL SYSTEM | OBJECTIVE OPTICAL SYSTEM | OBJECTIVE OPTICAL SYSTEM | OBJECTIVE OPTICAL SYSTEM |
| FIRST FOCUS POSITION | SECOND FOCUS POSITION | THIRD FOCUS POSITION | FOURTH FOCUS POSITION |

FIG.4
(A)
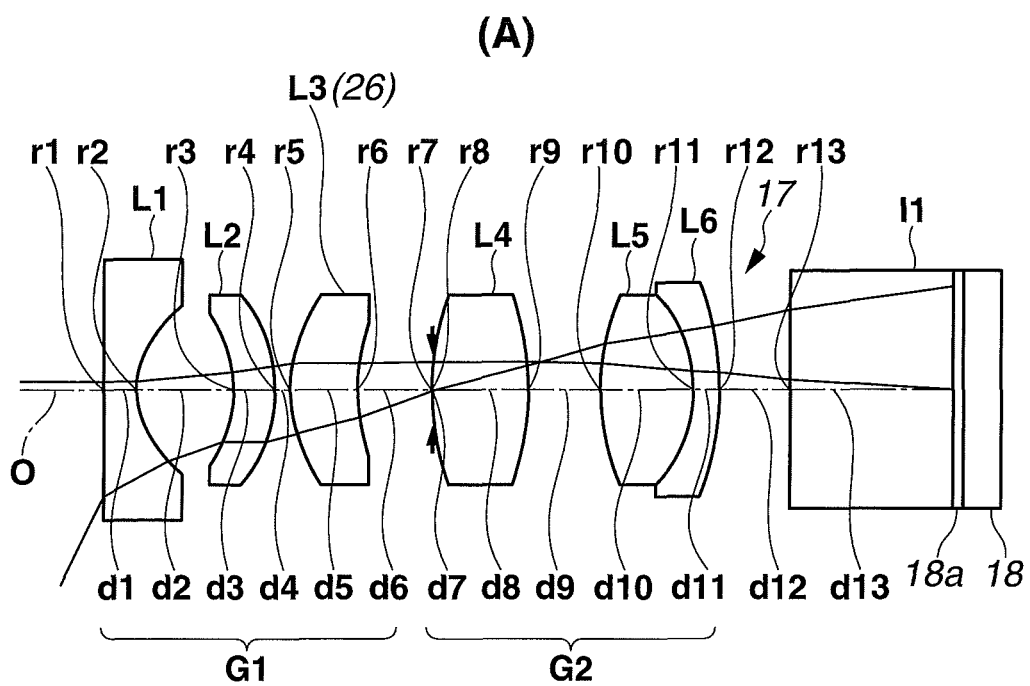
(B)
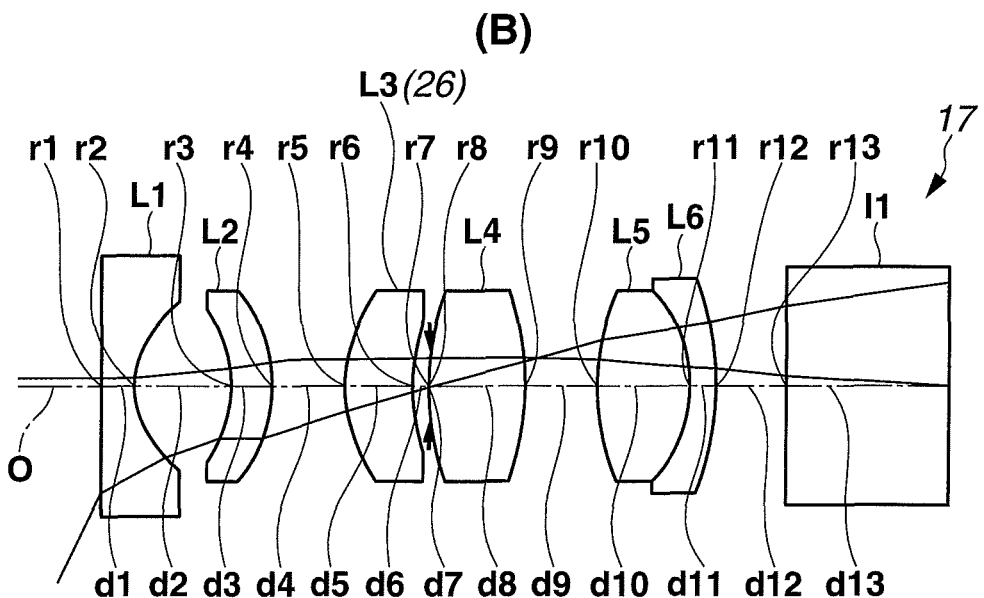

FIG.9
(A)
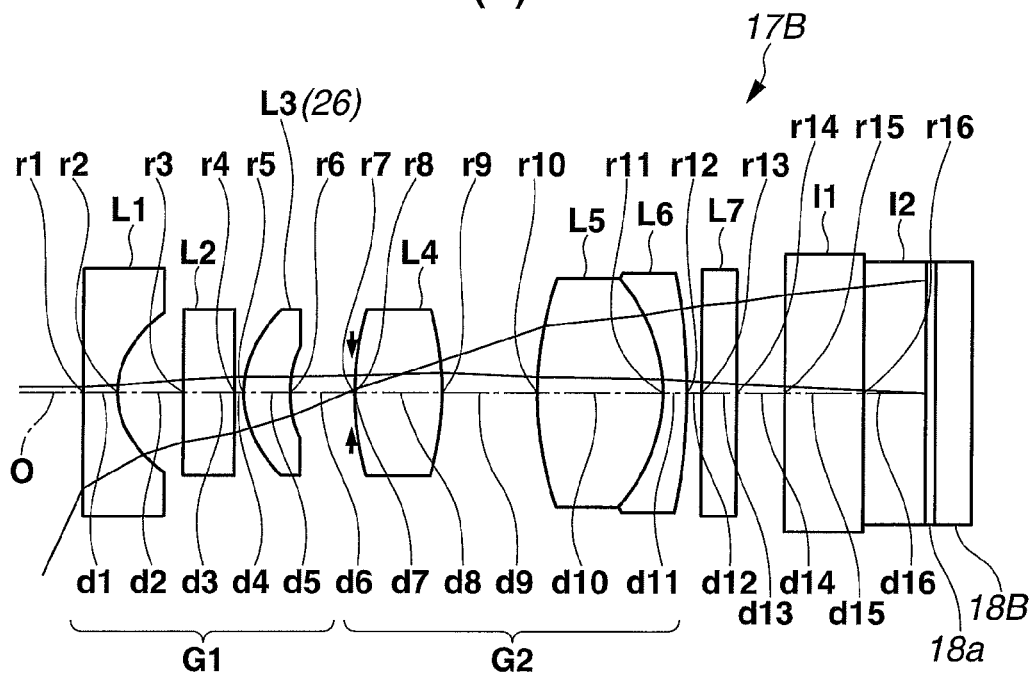
(B)
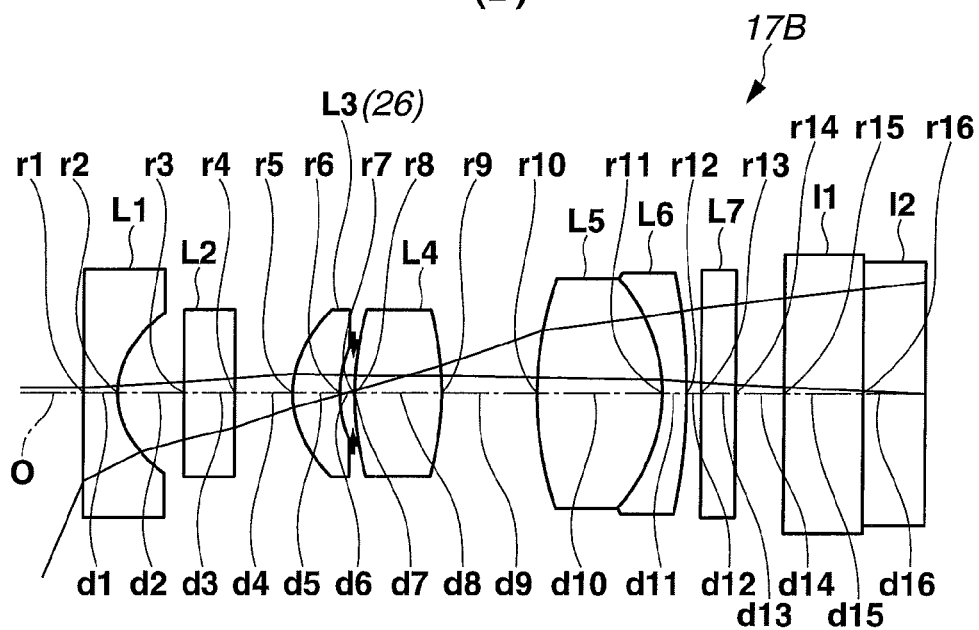

FIG.12
(A)
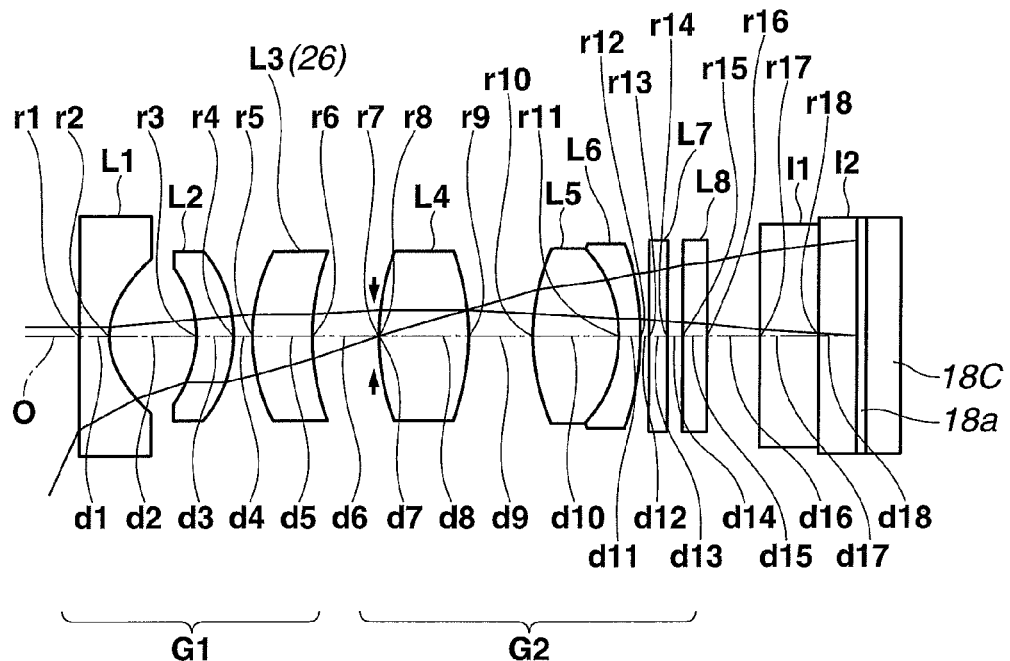
(B)
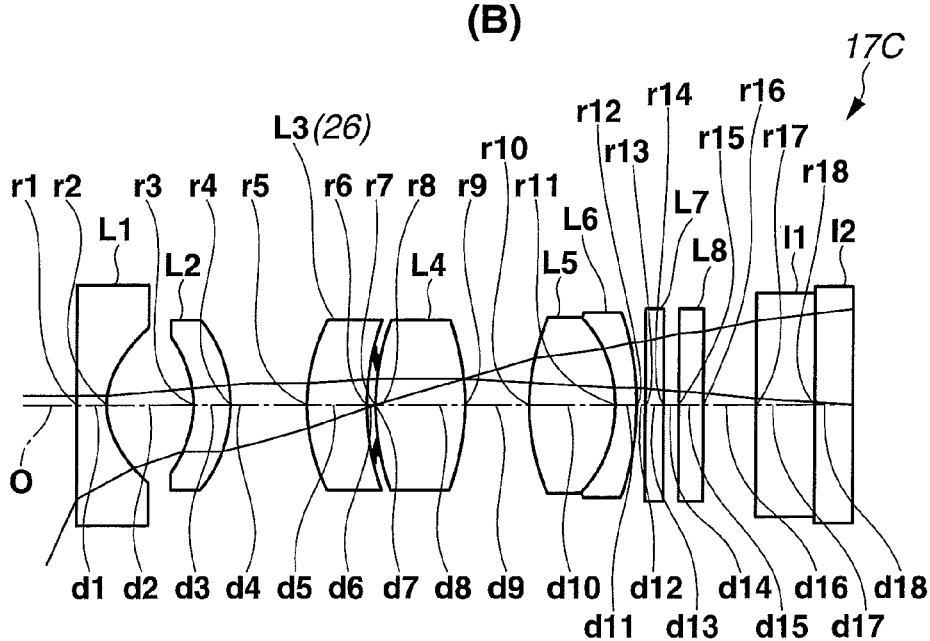

FIG.14
(A)
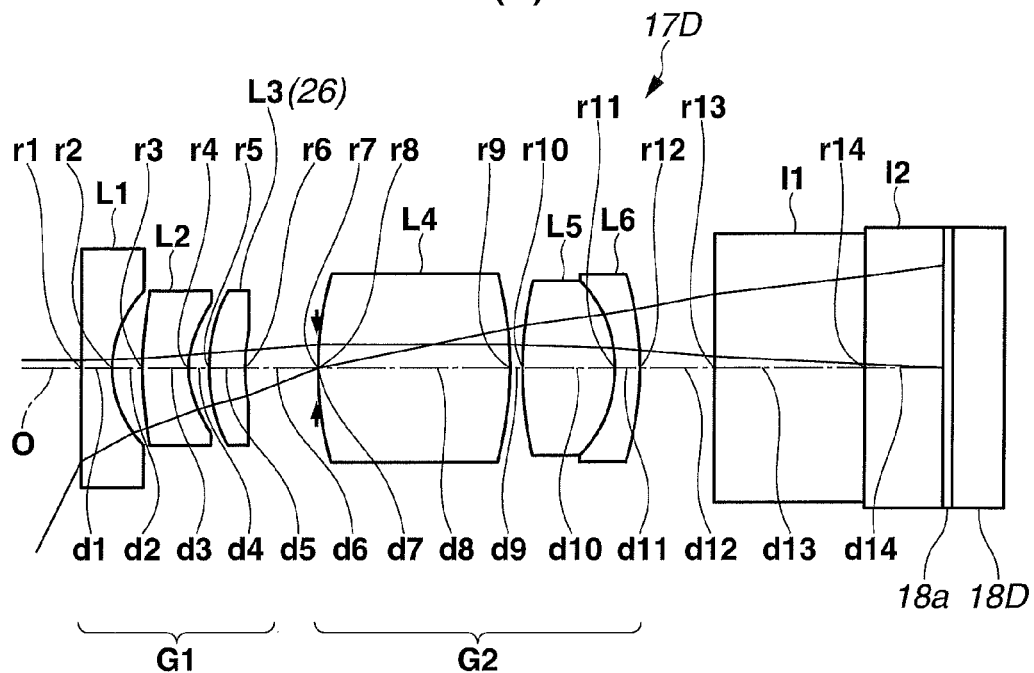
(B)
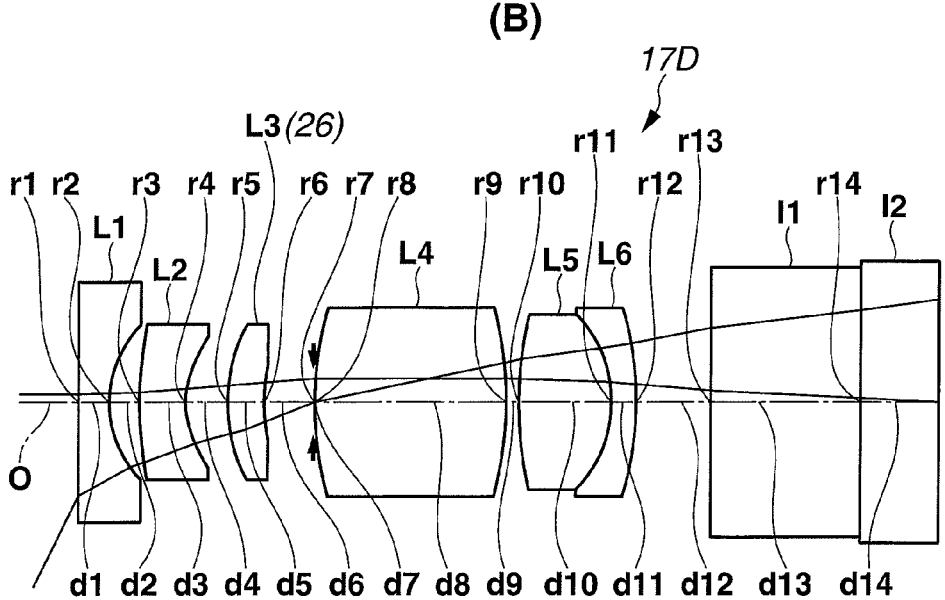

FIG.17
(A)
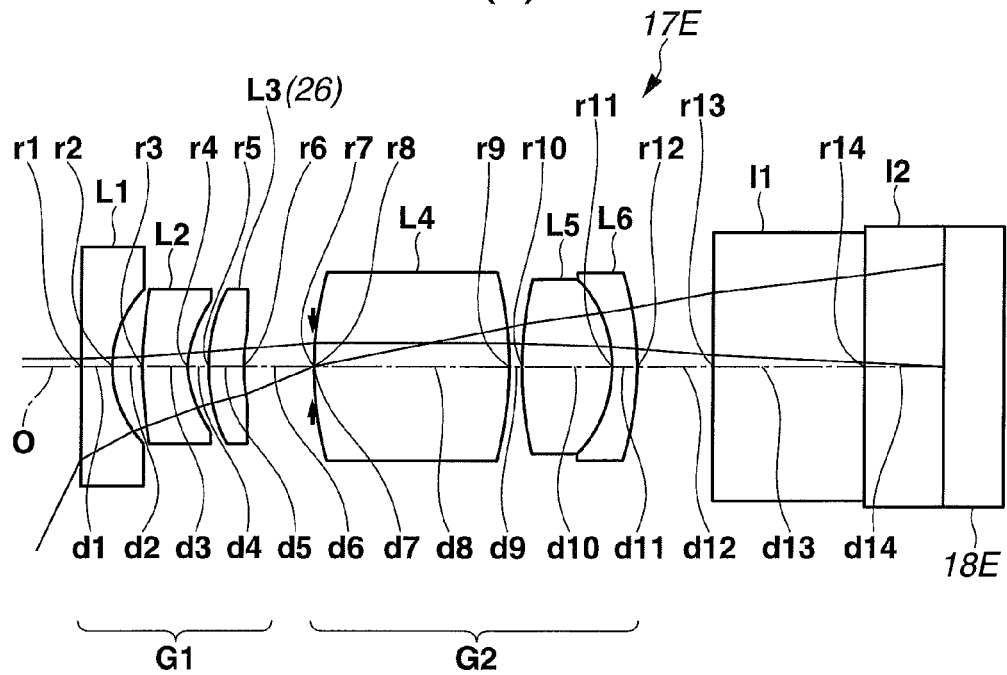
(B)
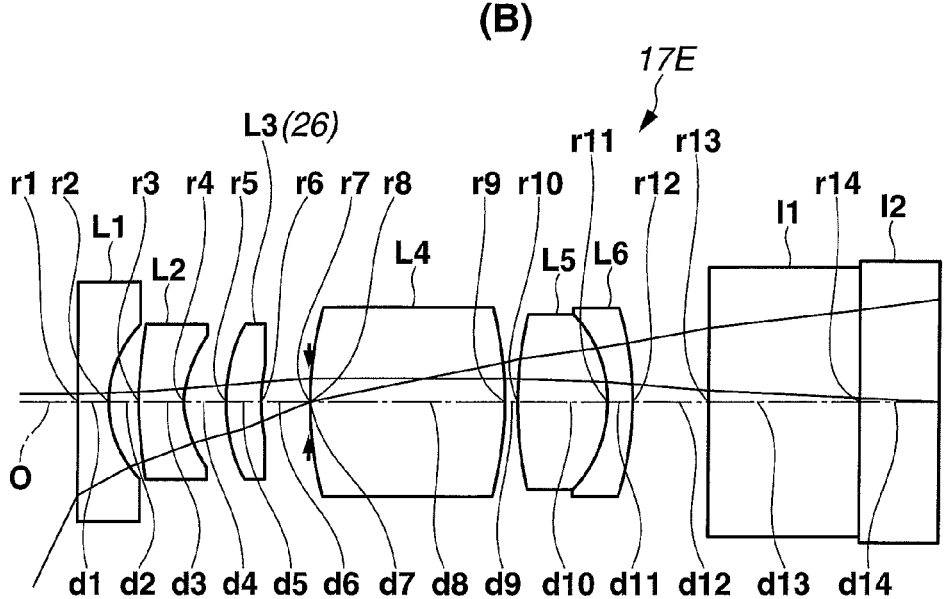

FIG.19
(A)
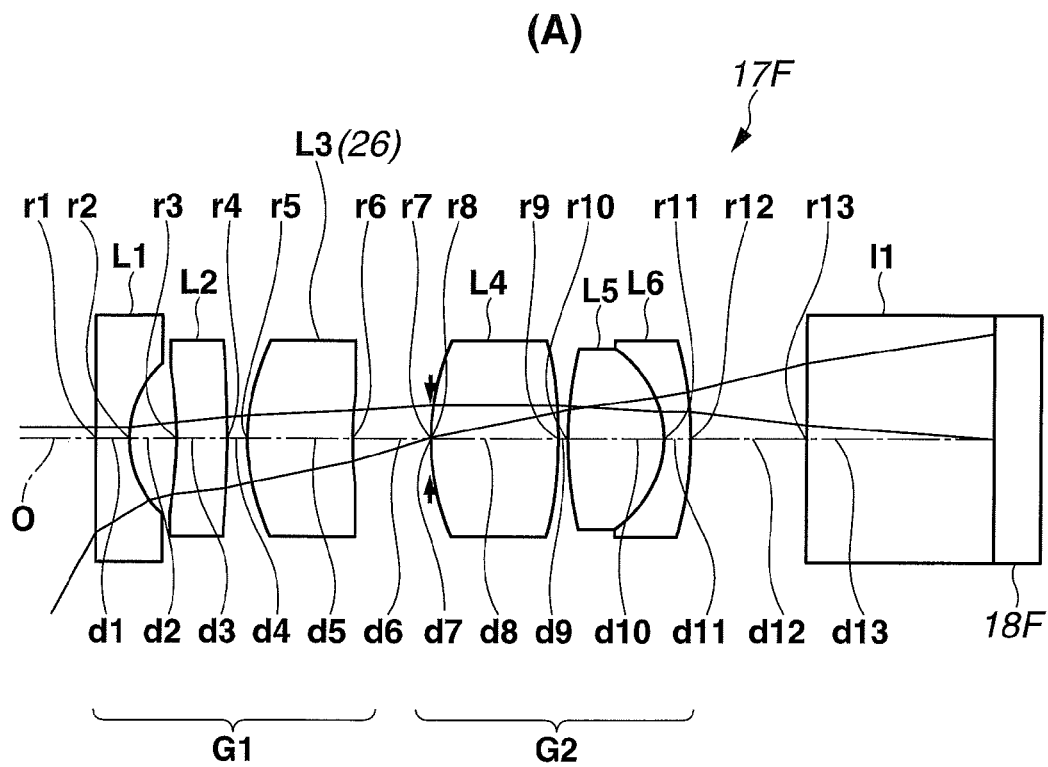
(B)
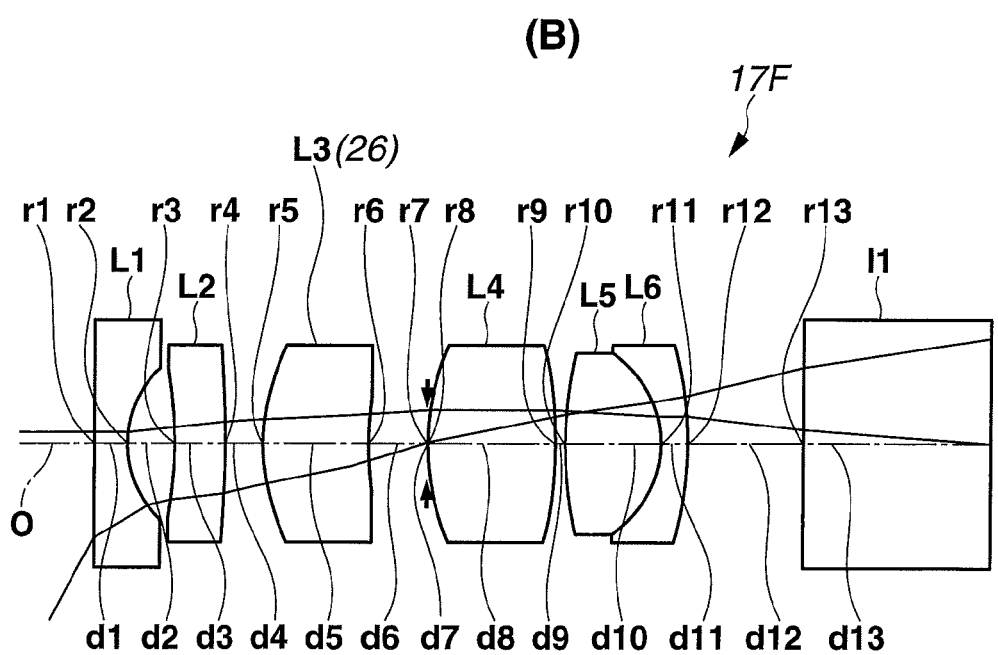

FIG.21
(A)
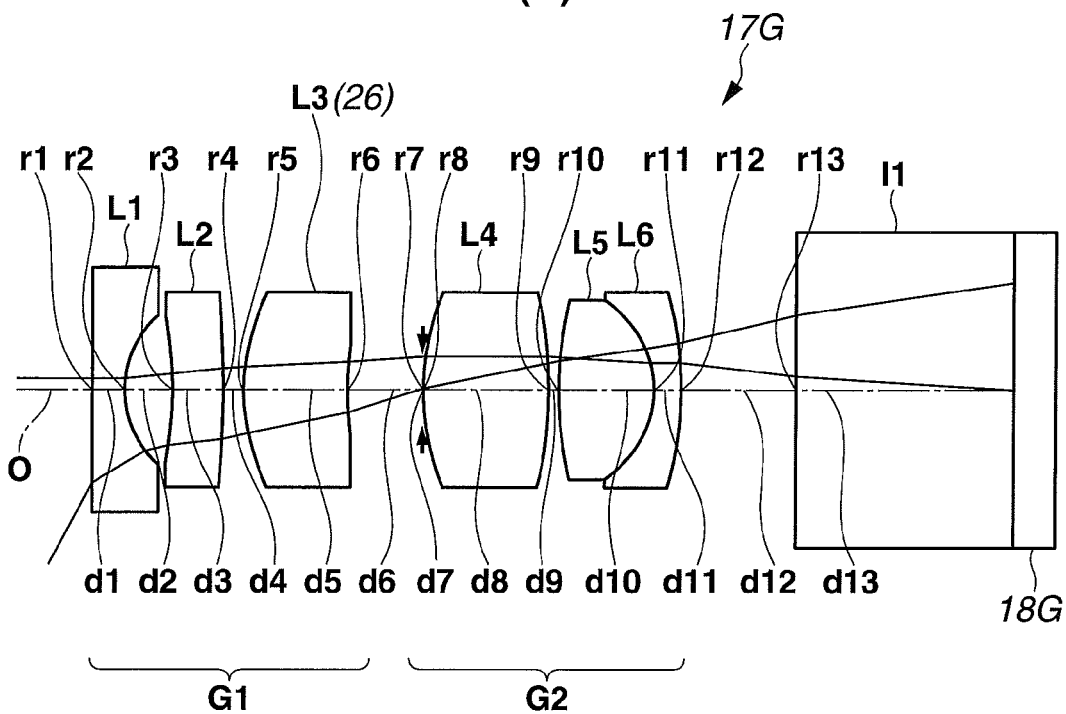
(B)
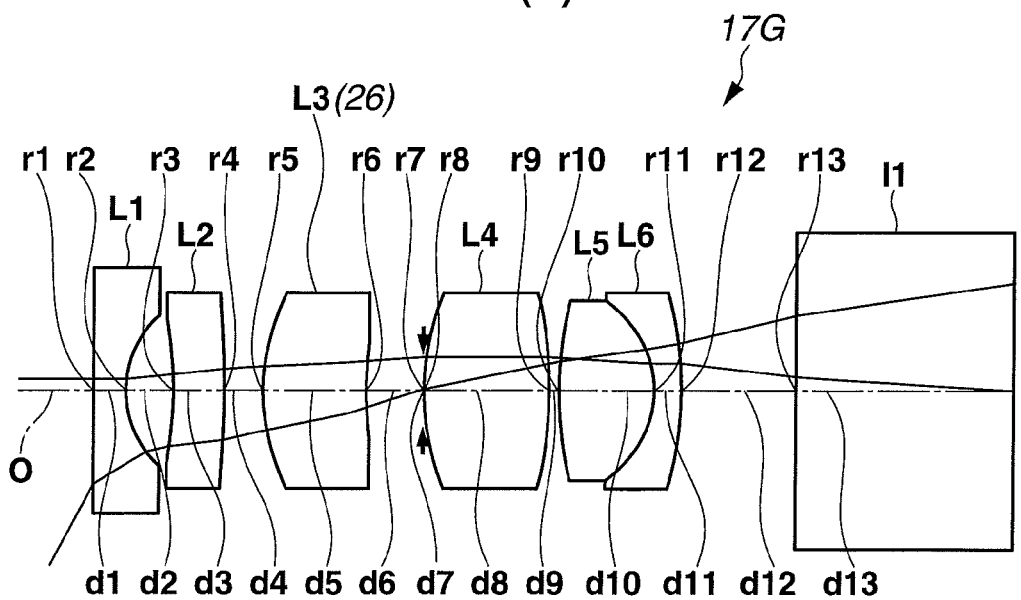

ENDOSCOPE APPARATUS

CROSS REFERENCE TO RELATED APPLICATION

This application is a continuation application of PCT/JP2012/066353 filed on Jun. 27, 2012 and claims benefit of Japanese Application No. 2011-175313 filed in Japan on Aug. 10, 2011, the entire contents of which are incorporated herein by this reference.

BACKGROUND OF THE INVENTION

1. Field of the Invention

The present invention relates to an endoscope apparatus having an autofocus function.

2. Description of the Related Art

In recent years, an endoscope including an image pickup unit employing a solid-state image pickup device has been widely used in a medical field.

There has also been proposed an endoscope including an optical system having an autofocus function to enable detailed observation of a diseased part and the like and an image pickup unit employing a solid-state image pickup device increased in the number of pixels.

For example, a conventional example of Japanese Patent Application Laid-Open Publication No. 2002-253489 discloses an endoscope apparatus that moves a part of lenses in an objective optical system to perform autofocus.

In the conventional example, when magnification controlling means is started up by operation of switching means, focus adjustment of the objective optical system is performed on a long focal length side in a variable focal length range of the objective optical system by focus controlling means started up in association with a control signal of the magnification controlling means.

In an examination or an observation by an endoscope, usually, a screening test is performed in a state in which the endoscope is focused on a far point side and, when a suspicious region is examined or observed in detail, operation for focusing the endoscope on a near point side is performed.

SUMMARY OF THE INVENTION

An endoscope apparatus according to an aspect of the present invention includes: an endoscope inserted into a tube cavity; an objective optical system mounted at a distal end portion of the endoscope and configured to form an image of an object in the tube cavity, the objective optical system including a focusing lens movable in an optical axis direction and satisfying conditional expressions (1) and (2); a solid-state image pickup device for color image pickup configured to pick up the image formed by the objective optical system, the solid-state image pickup device satisfying a conditional expression (3) below and a color separation filter being arranged for each pixel in the solid-state image pickup device; a focus adjusting mechanism configured to move the focusing lens and automatically adjust the objective optical system to a focused state; a moving range switching section configured to perform switching of a moving range of the focusing lens; a moving range limiting section configured to limit the moving range using a signal in association with the switching by the moving range switching section; and a setting information storing section configured to store information for adjusting the objective optical system to a plurality of focused states with the focus adjusting mechanism in the moving range limited by the moving range limiting section, $$0.8 < IH/f < 1.2 \qquad (1)$$

$$3.4 < f_{focus}/f < 15 \qquad (2)$$

$$550 < IH/P < 1200 \qquad (3)$$

where, IH represents a distance from a center in an image pickup region to a most distant position of the solid-state image pickup device, f represents a focal length of the objective optical system, $f_{focus}$ represents a focal length of the focusing lens, and P represents a pixel pitch of the solid-state image pickup device.

An endoscope apparatus according to another aspect of the present invention includes: an endoscope inserted into a tube cavity; an objective optical system mounted at a distal end portion of the endoscope and configured to form an image of an object in the tube cavity, the objective optical system including a focusing lens movable in an optical axis direction and satisfying conditional expressions (1) and (2) below; a monochrome solid-state image pickup device configured to pick up the image formed by the objective optical system, the solid-state image pickup device satisfying a conditional expression (3) below and generating a luminance signal for each pixel; a focus adjusting mechanism configured to move the focusing lens and automatically adjust the objective optical system to a focused state; a moving range switching section configured to perform switching of a moving range of the focusing lens; a moving range limiting section configured to limit the moving range using a signal in association with the switching by the moving range switching section; and a setting information storing section configured to store information for adjusting the objective optical system to a plurality of focused states with the focus adjusting mechanism in the moving range limited by the moving range limiting section, $$0.8 < IH/f < 1.2 \qquad (1)$$

$$3.4 < f_{focus}/f < 15 \qquad (2)$$

$$360 < IH/P < 800 \qquad (3)$$

where, IH represents a distance from a center in an image pickup region to a most distant position of the solid-state image pickup device, f represents a focal length of the objective optical system, $f_{focus}$ represents a focal length of the focusing lens, and P represents a pixel pitch of the solid-state image pickup device.

BRIEF DESCRIPTION OF THE DRAWINGS

FIG. 2 is a block diagram showing a configuration of a focus adjusting mechanism;

FIG. 3A is a sectional view showing a configuration of an image pickup unit portion;

FIG. 3B is a diagram showing a setting example of a current value for driving an actuator and a focus position of an objective optical system;

FIGS. 4(A) and 4(B) are sectional views of an objective optical system in states in which the objective optical system is set in a first focus position and a fourth focus position;

FIGS. 9(A) and 9(B) are sectional views of an objective optical system in states in which the objective optical system is set in the first focus position and a fifth focus position in a second embodiment of the present invention;

FIGS. 12(A) and 12(B) are sectional views of an objective optical system in states in which the objective optical system is set in the first focus position and the fourth focus position in a third embodiment of the present invention;

FIGS. 14(A) and 14(B) are sectional views of an objective optical system in states in which the objective optical system is set in the first focus position and a sixth focus position in a fourth embodiment of the present invention;

FIGS. 17(A) and 17(B) are sectional views of an objective optical system in states in which the objective optical system is set in the first focus position and the fifth focus position in the fifth embodiment;

FIGS. 19(A) and 19(B) are sectional views of an objective optical system in states in which the objective optical system is set in the first focus position and the fifth focus position in a sixth embodiment of the present invention;

FIGS. 21(A) and 21(B) are sectional views of an objective optical system in states in which the objective optical system is set in the first focus position and the sixth focus position in a seventh embodiment of the present invention.

DETAILED DESCRIPTION OF THE PREFERRED EMBODIMENTS

Embodiments of the present invention are explained below with reference to the drawings.

First Embodiment

Figure 1:
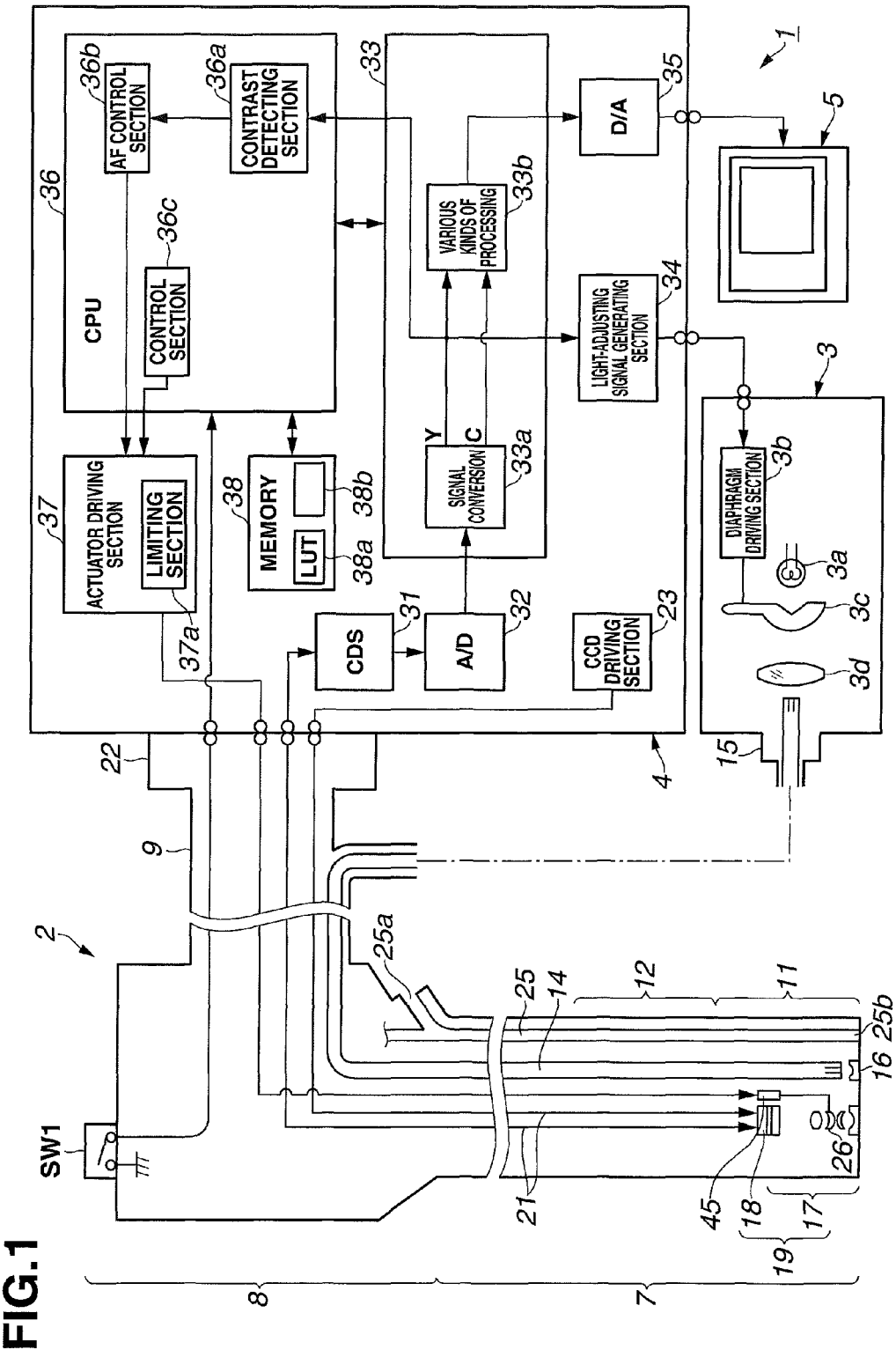
FIG. 1 is a diagram showing an overall configuration of an endoscope apparatus according to a first embodiment of the present invention.

As shown in FIG. 1, an endoscope apparatus 1 is configured by an endoscope 2 inserted into a tube cavity, a light source device 3 configured to supply illumination light for the endoscope 2, an image processing device (or a signal processing device) 4 configured to apply signal processing to a signal outputted from image pickup means mounted on the endoscope 2, and a monitor 5 functioning as display means for displaying an endoscopic image by receiving an input of a standard video signal (image signal) outputted from the image processing device 4.

The endoscope 2 in this embodiment includes an elongated insertion portion 7 inserted into a subject, an operation portion 8 provided at a rear end of the insertion portion 7 and gripped by an operator such as a surgeon to perform operation, and a cable portion 9 extended from the operation portion 8.

A rigid distal end portion 11 is provided at a distal end of the insertion portion 7. An image pickup unit 19 or the like that forms image pickup means is provided at the distal end portion 11.

A bendable bending portion 12 is provided adjacent to the distal end portion 11. The surgeon can bend the bending portion 12 in a desired direction by operating a not-shown bending operation knob in the operation portion 8.

A light guide 14 configured to transmit the illumination light is inserted through the insertion portion 7. A rear end side of the light guide 14 leads to a light guide connector 15 provided at an end thereof through the cable portion 9. The light guide connector 15 is connected to the light source device 3, whereby the illumination light is supplied from the light source device 3 to a rear end surface of the light guide 14.

The light source device 3 includes a lamp 3a functioning as a light source for generating the illumination light. Light of the lamp 3a is made incident on an incident end face of the light guide 14 in the light guide connector 15 through a focusing lens 3d after a transmitted light amount is adjusted by an opening of a diaphragm 3c driven by a diaphragm driving section 3b. The diaphragm driving section 3b drives the diaphragm 3c to adjust an opening amount of the diaphragm 3c, i.e., the transmitted light amount on the basis of a light-adjusting signal explained below.

The illumination light supplied from the light source device 3 is transmitted by the light guide 14 and emitted forward through an illumination lens 16 attached to a distal end face of the distal end portion 11 to illuminate an object such as a diseased part in the tube cavity.

At the distal end portion 11, an objective optical system 17 configured to form an optical image of the illuminated object is provided adjacent to the illumination lens 16. The image pickup unit 19 is configured by the objective optical system 17 and, for example, a charge coupled device (abbreviated as CCD) 18 functioning as a solid-state image pickup device, an image pickup surface (a photoelectric conversion surface) of which is arranged in an image-forming position of the objective optical system 17.

The CCD 18 in this embodiment is a CCD of a mosaic color filter type including a mosaic color filter 18a (see FIG. 4(A)) such as a complementary color system, for example, as a color separation filter that optically separates colors.

One end of a signal cable 21 is connected to the image pickup unit 19. The signal cable 21 inserted through the insertion portion 7 is further inserted through the cable portion 9. The other end of the signal cable 21 is connected to a signal connector 22 at a rear end of the cable portion 9.

The signal connector 22 is connected to the image processing device 4, whereby the CCD 18 is driven by a CCD driving signal from a CCD driving section 23 provided on an inside of the image processing device 4. The CCD 18 outputs a photoelectrically converted image pickup signal as an output signal.

The image pickup signal is subjected to signal processing by a signal processing section in the image processing device 4 and a standard video signal (image signal) is generated. An endoscopic image is displayed on the monitor 5.

A channel 25 for enabling various treatment instruments to be inserted is provided in the insertion portion 7.

The surgeon can project a distal end side of a treatment instrument from a distal end opening 25b opened at the distal end portion 11 and can sample a diseased part tissue and perform treatment such as excision by inserting the treatment instrument from a treatment instrument insertion port 25a near a front end of the operation portion 8.

In this embodiment, the objective optical system 17 configuring the image pickup unit 19 includes a movable focusing lens 26. The focusing lens 26 is not limited to be formed by a single lens and may be formed by a single cemented lens.

In this embodiment, the objective optical system 17 that forms an image at a far wider angle compared with a general camera or the like is used. When a focal length of the objective optical system 17 is represented as f, a focal length of the focusing lens 26 is represented as $f_{focus}$, and a distance (image height) from a center position in an image pickup region of the CCD 18 to a most distant position is represented as IH, the objective optical system 17 satisfies conditional expressions (1) and (2) below.

$$0.8 < IH < f < 1.2 \quad (1)$$

$$3.4 < f_{focus} g < 15 \quad (2)$$

When a pixel pitch in a horizontal direction and a vertical direction of the CCD 18 is represented as P, the CCD 18 for color image pickup including the mosaic color filter 18a functioning as a color separation filter satisfies conditional expression (3) below.

$$550 < IH/P < 1200 \quad (3)$$

In this embodiment, the endoscope apparatus 1 includes a focus adjusting mechanism 27 (see FIG. 2) configured to move the focusing lens 26 and automatically adjust the objective optical system 17 to a focused state. The conditional expressions (1) to (3) are satisfied in second to fourth embodiments explained below as well.

When an examination or an observation is performed using the endoscope 2 by moving the focusing lens 26 with the focus adjusting mechanism 27, focus control is automatically performed such that an object such as a diseased part at an arbitrary distance in a predetermined distance range can be observed by the objective optical system 17 in the focused state.

An image pickup signal outputted from the CCD 18 is inputted to a correlated double sampling circuit (abbreviated as CDS circuit) 31 that forms the signal processing section in the image processing device 4. After CDS processing, the image pickup signal is converted into a digital image signal by an A/D converter 32 and inputted to an image processing section 33.

The image processing section 33 includes a signal converting circuit 33a configured to convert an input signal into image signals of a luminance signal Y and a color signal C. The image processing section 33 outputs the luminance signal Y to a light-adjusting signal generating section 34. The light-adjusting signal generating section 34 generates a light-adjusting signal and outputs the light-adjusting signal to the diaphragm driving section 3b of the light source device 3.

The digital image signal (video signal) outputted from the image processing section 33 is converted into an analog image signal by a D/A converter 35 and thereafter outputted to the monitor 5. An endoscopic image corresponding to the image signal is displayed on the monitor 5.

The image processing section 33 outputs the luminance signal Y to a contrast detecting section 36a of a CPU 36 that forms control means. The contrast detecting section 36a configured by the CPU 36 detects contrast of the image from a luminance value in the inputted luminance signal Y. Information concerning the detected contrast is inputted to an autofocus control section (an AF control section in FIG. 1) 36b of the CPU 36 and used for autofocus control.

The autofocus control section 36b moves the focusing lens 26 via an actuator driving section 37 and automatically sets the objective optical system 17 in a focused state.

In this embodiment, in order to effectively prevent a malfunction due to autofocus and improve speed of the autofocus (set the objective optical system 17 in the focused state in a short time), a limiting section 37a is provided in the actuator driving section 37 as moving range limiting means for limiting focusing moving ranges (simply abbreviated as moving ranges), in which the focusing lens 26 is movable, to a plurality of moving ranges, more specifically, two moving ranges. The limiting section 37a limits the moving ranges using a signal in association with switching of moving range switching means explained below.

That is, in the case of one moving range of the two moving ranges, the objective optical system 17 can be focused on an object in a region on a far point side. In the case of the other moving range, the objective optical system 17 can be focused on the object in a region on a near point side.

A control section 36c is provided in the CPU 36 as control means for controlling an operation of the limiting section 37a.

In this embodiment, a change-over switch SW1 that forms moving range switching means for manually performing switching of the moving range of the focusing lens 26 is provided in the operation portion 8 of the endoscope 2. An operation signal of the change-over switch SW1 is inputted to the CPU 36.

The surgeon can select the one moving range and perform operation for switching the one moving range to the other moving range by operating the change-over switch SW1. When the one moving range is selected, the autofocus control section 36b of the CPU 36 performs autofocus control in the one moving range. When the operation for switching the one moving range to the other moving range is performed, the autofocus control section 36b performs the autofocus control in the other moving range. The change-over switch SW1 may be configured by a lever.

In this embodiment, a plurality of focus positions (first to fourth focus positions in FIG. 6) different from one another are registered in advance as focus positions for setting the objective optical system 17 in the focused state. A memory 38 functioning as setting information storing means for storing positioning information for the focusing lens 26 for setting the focusing lens 26 in the registered plurality of focus positions is provided.

The memory 38 stores information concerning a moving amount or a driving signal amount (a current value) of the focusing lens 26 necessary for moving the focusing lens 26 in a direction of an optical axis O (see FIG. 4(A)) with an actuator 45 and setting the objective optical system 17 in each of the first to fourth focus positions.

FIG. 3B shows an example in which positioning of the focusing lens 26 is performed according to current values Ia, Ib, Ic, and Id for driving the actuator 45 and the objective optical system 17 is set in each of the first to fourth focus positions. In this case, Ia<Ib<Ic<Id.

In the memory 38, the information is stored as a lookup table (LUT) 38a in which the first to fourth focus positions and four current values are associated with each other.

Figure 6:
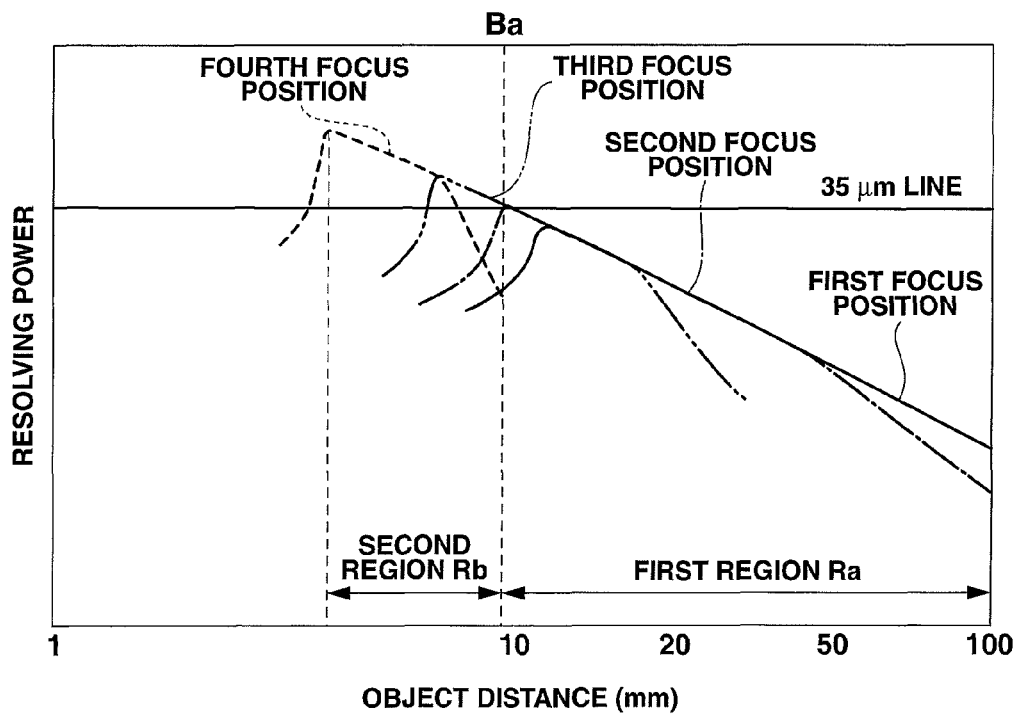
FIG. 6 is a diagram showing a relation between an object distance and resolving power in states in which the objective optical system is set in respective focus positions shown in FIGS. 4(A) and 4(B)

Respective kinds of position information in an optical axis direction of the focusing lens 26 in a state in which the objective optical system 17 is set in each of the first to fourth focus positions shown in FIG. 6 may be stored as setting information.

In this embodiment, when the objective optical system 17 is set in one focus position among the first to fourth focus positions by autofocus, the CPU 36 performs control to store set information in the memory 38 in time series.

In other words, the CPU 36 stores, in a focus position information storing section 38b in the memory 38, information concerning a focus position where the objective optical system 17 is currently set. The autofocus control section 36b performs autofocus control referring to the current focus position information.

In the following explanation, the setting information is assumed to be driving signal amounts.

As explained above, the moving ranges of the focusing lens 26 are limited to the two moving ranges. Therefore, when the focusing lens 26 is driven in the respective moving ranges, the driving signal amounts only have to be two driving signal amounts respectively corresponding to the two focus positions.

That is, when the focusing lens 26 is focused on an object in a first region Ra on a far point side from the object as shown in FIG. 6, the focusing lens 26 is adjusted to be positioned such that the objective optical system 17 is in the focused state in the first focus position or the second focus position. When the focusing lens 26 is focused on the object in a second region Rb on a near point side from the object, the focusing lens 26 is adjusted to be positioned such that the objective optical system 17 is in the focused state in the third focus position or the fourth focus position.

Therefore, the autofocus control section 36b performs, referring to the setting information of the LUT 38a and the current focus position information of the focus position information storing section 38b, the autofocus control such that the objective optical system 17 is in the focused state in the case of one driving signal amount with which contrast is higher.

In this embodiment, the endoscope apparatus 1 includes the objective optical system 17, an angle of view of which hardly changes even when the focusing lens 26 is moved in the moving ranges. More specifically, the objective optical system 17 is configured such that change in the angle of view can be suppressed to be within 5% when a focus position is changed by the autofocus control.

In this way, in this embodiment, the endoscope apparatus 1 is configured to perform extremely simple autofocus control.

FIG. 2 shows a configuration of the focus adjusting mechanism 27. The focus adjusting mechanism 27 is configured by the autofocus control section 36b configured to perform control of autofocus according to the contrast information of the contrast detecting section 36a and the setting information of the memory 38 shown in FIG. 1, an actuator driving section 37 driven on the basis of the autofocus control section 36b, and the actuator 45 configured to move the focusing lens 26 with the actuator driving section 37.

FIG. 3A shows a configuration of the image pickup unit 19 including the actuator 45 provided at the distal end portion 11. FIGS. 4(A) and 4(B) show sectional views of the objective optical system 17 in representative two focus positions in the case in which the focusing lens 26 is moved. FIG. 4(A) shows a sectional view in the case of the first focus position. FIG. 4(B) shows a sectional view in the case of the fourth focus position.

As shown in FIG. 4(A), the objective optical system 17 is configured by, in order from an object side, a front group G1 including the focusing lens 26 (L3) and a rear group G2 including an aperture diaphragm (hereinafter simply referred to as diaphragm).

The front group G1 is configured by a concave lens L1, a convex lens L2, and the focusing lens 26 (L3). The rear group G2 is configured by a diaphragm, a convex lens L4, and a cemented lens of a convex lens L5 and a concave lens L6. An optical element (an optical filter) I1 is arranged behind the rear group G2. The image pickup surface of the CCD 18 is arranged via the mosaic color filter 18a to be set in contact with a rear surface of the optical element I1. Note that the rear group G2 may be defined to include the optical element I1.

Numerical value data of the objective optical system 17 in this embodiment is shown below.

| Numerical value data in the first embodiment | | | | |
|---|---|---|---|---|
| Surface number | Curvature radius | Surface interval | Refractive index | Abbe number |
| Object surface | ∞ | D0 | | |
| 1 | ∞ | 0.3 | 1.81991 | 44.36 |
| 2 | 0.9274 | 0.887 | | |
| 3 | −1.2823 | 0.378 | 1.88815 | 40.76 |
| 4 | −1.3551 | D4 | | |
| 5 | 1.7247 | 0.598 | 1.50349 | 56.42 |
| 6 | 2.2643 | D6 | | |
| 7 (Diaphragm) | ∞ | 0.026 | | |
| 8 | 2.5456 | 0.897 | 1.48915 | 70.23 |
| 9 | −2.3398 | 0.642 | | |
| 10 | 2.3577 | 0.879 | 1.48915 | 70.23 |
| 11 | −1.2741 | 0.227 | 1.93429 | 18.9 |
| 12 | −2.7451 | 0.6816 | | |
| 13 | ∞ | 1.5 | 1.51825 | 64.14 |
| (Image surface) | ∞ | | | |

| | First focus position | Second focus position | Third focus position | Fourth focus position |
|---|---|---|---|---|
| D0 | 21.8 | 15.4 | 9.65 | 4.88 |
| D4 | 0.156 | 0.236 | 0.386 | 0.706 |
| D6 | 0.65 | 0.57 | 0.42 | 0.1 |
| Width of depth of field (mm) | 10.8 to 100 or larger | 8.8 to 49 | 6.42 to 17.9 | 3.74 to 6.78 |
| Angle of view (°) | | | | |
| Pitch P | 1.3 μm | | | |
| IH | 0.94 | | | |
| IH/P | 723 | | | |
| f | 1 | | | |
| IH/f | 0.94 | | | |
| Resolution | 34.4 μm (At time of 8.8 mm) | | | |
| $f_{focus}$ | 10.484 | | | |
| $f_{focus}/f$ | 10.48 | | | |

The refractive index and the Abbe number are values with respect to an e line.

D0 indicates a distance from an object surface to a first surface of the objective optical system 17.

As shown in FIG. 3A, the lenses L1 and L2 of the front group G1 are attached to the lens barrel 41a. The movable focusing lens 26 (L3), the diaphragm, and the convex lens L4 and the cemented lenses L5 and L6 of the rear group G2 are attached to a lens barrel 41b that fits in the lens barrel 41a. The optical element I1 and the CCD 18 are attached to a lens barrel 41c that fits in a rear end side of the lens barrel 41b.

The focusing lens 26 is attached to a movable lens barrel 42 that fits in an inner peripheral surface of the lens barrel 41b. The movable lens barrel 42 is integrally coupled to an arm 44 that pierces through a groove for movement 43 provided in the lens barrel 41b. A rod 46 projecting from the actuator 45 is coupled to the arm 44.

The actuator 45 is connected to the actuator driving section 37 via a signal line 47. The actuator 45 changes, with operation of the change-over switch SW1, a projecting amount or a moving amount from a reference position of the rod 46 according to a driving signal applied from the actuator driving section 37 under control by the CPU 36. The focusing lens 26 moves along the direction of the optical axis O according to the change in the projecting amount or the moving amount of the rod 46. In the case of FIG. 3A, as a current amount of the driving signal for driving the actuator 45 is larger, a moving amount for moving the focusing lens 26 to the CCD 18 side is larger.

Note that the signal cable 21 connected to a back of the CCD 18 is connected to the CCD driving section 23 and the CDS circuit 31.

Figure 5:
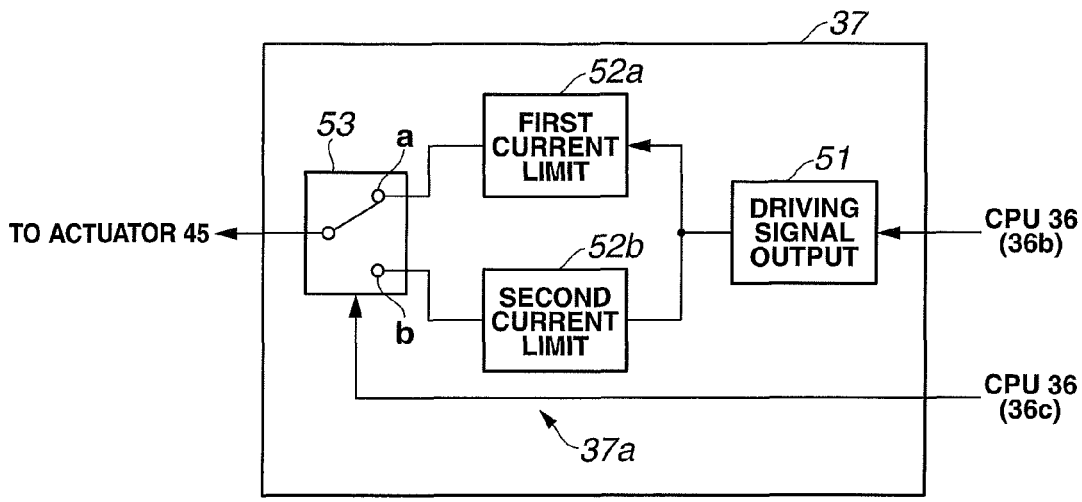
FIG. 5 is a block diagram showing a configuration for limiting a driving signal for an actuator driving section and limiting moving ranges by a focusing lens to two moving ranges.

FIG. 5 shows a configuration example of the actuator driving section 37. According to operation of the change-over switch SW1, the autofocus control section 36b of the CPU 36 causes a driving signal output section 51, which configures the actuator driving section 37, to output a driving signal.

The driving signal drives the actuator 45 via a change-over switch 53, contacts a and b of which are respectively connected to respective output ends of a first current limiting circuit 52a and a second current limiting circuit 52b. The change-over switch 53 switches, according to an operation signal of the change-over switch SW1, a control signal by the control section 36c of the CPU 36 to turn on the contact a or b.

When the objective optical system 17 is switched to be auto-focused on the object in the first region Ra on the far point side in FIG. 6 by the change-over switch SW1, the driving signal drives the actuator 45 via the first current limiting circuit 52a and the contact a and limits the moving range of the focusing lens 26 within a first moving range Ka such that the focusing lens 26 is focused on one of a plurality of focus positions in the first region Ra on the far point side.

When the second region Rb on the near point side is selected, the driving signal drives the actuator 45 via the second current limiting circuit 52b and the contact b and limits the moving range of the focusing lens 26 within a second moving range Kb such that the focusing lens 26 is focused in the second region Rb on the near point side.

The first current limiting circuit 52a and the second current limiting circuit 52b limit a current value of the inputted driving signal. More specifically, the first current limiting circuit 52a limits the current value within a first current value (in the case of a table in FIG. 3b, a current value Ib) such that the focusing lens 26 can move only in the first moving range Ka close to the object side in the moving range.

In the first moving range Ka, the first focus position and the second focus position of the objective optical system 17 are within a range in which the focus positions can be set. However, the third focus position and the fourth focus position are outside the range in which the focus positions can be set.

On the other hand, the second current limiting circuit 52b limits the current value to a second current value (in the case of FIG. 3B, a current value larger than the current value Ib and including current values Ic and Id) such that the focusing lens 26 can move only in the second moving range Kb far from the object side in the moving range.

In the second moving range Kb, the third focus position and the fourth focus position of the objective optical system 17 are within a range in which the focus positions can be set. However, the second focus position and the first focus position are outside a range in which the focus positions can be set.

A projecting amount of the rod 46 of the actuator 45 from the reference position is regulated by a not-shown elastic member such as a spring. A projecting amount of the rod 46 can be adjusted against an elastic force of the elastic member according to a value of a current value of the driving signal applied to the actuator 45.

In FIG. 3A, a full moving range K, the first moving range Ka, and the second moving range Kb of the focusing lens 26 are shown. A boundary between the first moving range Ka and the second moving range Kb is B.

In this way, the moving range of the focusing lens 26 is divided into the two moving ranges Ka and Kb and limited to the divided respective moving ranges. Consequently, it is possible to effectively prevent a malfunction when focus control is automatically performed. A moving amount of the focusing lens 26 in the moving ranges Ka and Kb can be set smaller than a moving amount set when the moving range is not limited. Therefore, it is possible to improve speed of autofocus.

When the objective optical system 17 is automatically adjusted to a focus position by the focus adjusting mechanism 27 according to the setting information stored in the memory 38 in the moving range Ka on the far point side in which the moving range is limited in this way, resolving power on the optical axis of the objective optical system 17 has resolving power equal to or larger than 35 μm in a focus position where a distance between the objective optical system 17 and the object is equal to or smaller than 15 mm. When a range in which MTF (modulation transfer function) of a spatial frequency $1/(3 \times P)$ on the optical axis of the objective optical system 17 is equal to or higher than 10% is defined as depth of field width (simply, width of depth of field), the boundary B between the moving ranges Ka and Kb (see FIG. 3A) is set such that the objective optical system 17 has width of depth of field equal to or larger than 5 mm. Consequently, predetermined observation conditions suitable for smoothly performing an endoscopy are satisfied. An object distance corresponding to the boundary B (an object distance in a boundary between the first region Ra and the second region Rb) is indicated by a dotted line Ba in FIG. 6.

As it is seen from a characteristic of resolving power with respect to an object distance in FIG. 6, in a state of the second focus position on the far point side, the objective optical system 17 has resolving power equal to or higher than 35 μm near 10 mm and has width of depth of field equal to or larger than 5 mm.

Figure 7:
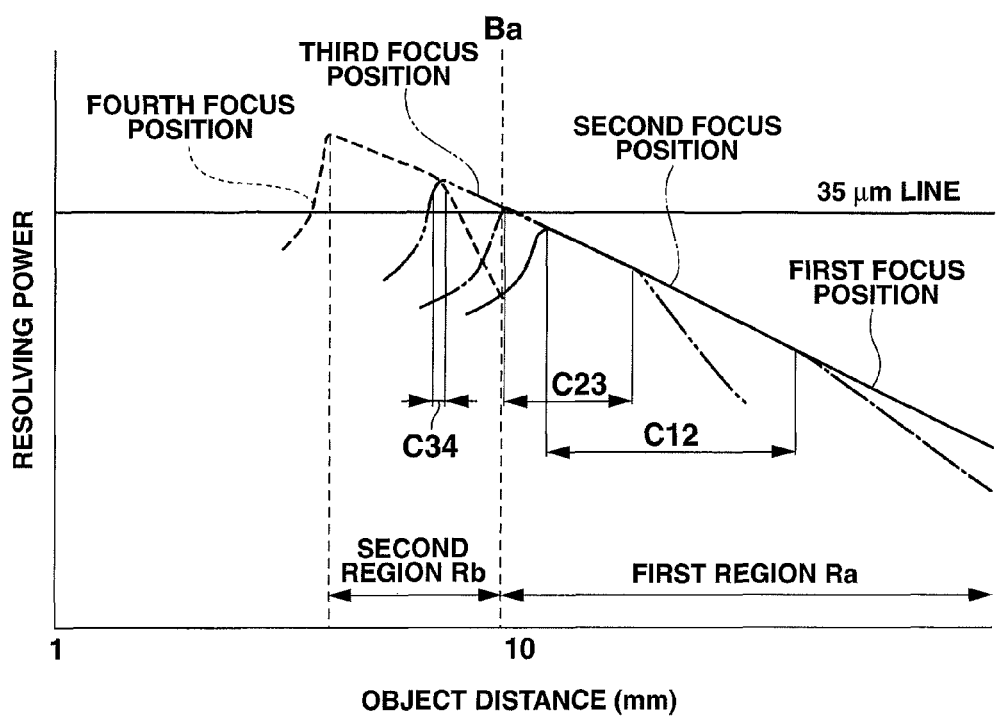
FIG. 7 is a diagram showing an overlapping range of widths of depth of field in adjacent focus positions.

A 35 μm line shown in FIGS. 6 and 7 indicates resolving power with which white and black of a 35 μm pitch can be identified. It is seen that resolving power exceeding the 35 μm line is satisfied in a focus position in the first region Ra (in the case of the second focus position).

In this embodiment, as it is seen from the characteristic of the resolving power in FIG. 6, when the objective optical system 17 is set in a plurality of focus positions in Ra and Rb corresponding to the two moving range Ka and Kb, as the objective optical system 17 is set in a focus position closer to the far point side, overlapping width of depth of field of adjacent focus positions is set larger. FIG. 7 shows a degree of the overlapping width of the widths of depth of field.

When overlapping width of widths of depth of field of the first focus position and the second focus position is represented as C12, overlapping width of widths of depth of field of the second focus position and the third focus position is represented as C23, and overlapping width of widths of depth of field of the third focus position and the fourth focus position is represented as C34, the overlapping widths are set to have a relation C12>C23>C34.

By setting the overlapping widths in this way, in the focus position closer to the far point side, width of depth of field of the focus position can be set wider. Even when the distal end portion 11 of the endoscope 2 is moved and a focus state is shifted from one focus position to the other focus position adjacent to the one focus position according to the movement, the objective optical system 17 can be smoothly moved to and set in a focused position of the other focus position without a main part being blurred. In the other embodiments explained below, as explained with reference to FIG. 7, overlapping width of widths of depth of field is set to be larger in a focus position closer to the far point side.

An operation in this embodiment is explained with reference to FIG. 8.

The endoscope apparatus 1 is set as shown in FIG. 1 and a power supply is turned on to set the endoscope apparatus 1 in an operation state. In first step S1, the CPU 36 sets, in processing of initial setting, the focusing lens 26 in a state in which autofocus control is performed.

As shown in step S2, as an initial state, the CPU 36 performs the autofocus control such that the change-over switch SW1 sets the focusing lens 26 in a focus region on the first region Ra side within the first moving range Ka.

As shown in step S3, the objective optical system 17 is adjusted in autofocus by the focusing lens 26 to be set in the first focus position or the second focus position as a focused state. As shown in step S4, current focus position information in the case in which the objective optical system 17 is auto-focused is stored in the focus position information storing section 38b of the memory 38. Therefore, when the objective optical system 17 moves from the current focus position to another focus position, the objective optical system 17 can be easily set in the other focus position. Note that an encoder may be provided to make it possible to acquire information concerning a driving state of the actuator 45 or a setting position of the focusing lens 26 or use the encoder to check the setting position.

As shown in step S5, in a state in which the objective optical system 17 is set in the first focus position or the second focus position, an endoscopic image is displayed on the monitor 5 in a predetermined display size.

When the surgeon inserts the endoscope 2 into a tube cavity and performs rough screening for presence or absence of a lesion, i.e., a screening test while moving the distal end portion 11, the objective optical system 17 is set in the first focus position or the second focus position having relative wide width of depth of field. Therefore, it is possible to smoothly perform the screening.

When the surgeon intends to observe in detail a diagnosis target region that is likely to be a legion, the surgeon brings the distal end portion 11 to the region and performs operation for pressing the change-over switch SW1 such that the surgeon can observe the region more in detail.

As a focused state on the far point side before the change-over switch SW1 is operated, the objective optical system 17 can be set in the second focus position. In a state in the second focus position, the objective optical system 17 satisfies predetermined observation conditions that the objective optical system 17 has resolving power equal to or higher than 35 μm and width of depth of field thereof is equal to or larger than 5 mm in a focus position at a distance equal to or smaller than 15 mm from the diagnosis target region. The width of depth of field is more desirably equal to or larger than 10 mm.

Therefore, the surgeon can sufficiently identify or grasp a state of the diagnosis target region before operating the change-over switch SW1 and can smoothly shift to a process for observing the observation target region more in detail according to the operation of the switching by the change-over switch SW1. When the predetermined observation conditions are not satisfied, for example, when only resolving power lower than 35 μm can be attained, in the focused state on the far point side, resolving power for the screening test cannot be provided. Therefore, it is difficult to smoothly perform the screening test.

As shown in step S6, the CPU 36 monitors whether the change-over switch SW1 is operated. When determining that the change-over switch SW1 is not operated (No in step S6), the CPU 36 returns to step S2.

On the other hand, when determining that the change-over switch SW1 is operated (Yes in step S6), in step S7, the CPU 36 moves the focusing lens 26 within the second moving range Kb and performs control to perform autofocus control to set the second region Rb side as a focus region.

As shown in step S8, the objective optical system 17 is adjusted in autofocus by the focusing lens 26 such that the objective optical system 17 is set in the third focus position or the fourth focus position as a focused state. As shown in step S9, current focus position information in the case in which the objective optical system 17 is auto-focused is stored in the memory 38.

As shown in step S10, in a state in which the objective optical system 17 is set in the third focus position or the fourth focus position, an endoscopic image is displayed on the monitor 5 in a predetermined display size.

When the surgeon observes a diagnosis target region on the near point side, a display size of the diagnosis object region does not fluctuate from the display size in the case of the far point side. The surgeon can observe the diagnosis object region with an endoscopic image having high resolving power.

As explained above, in this embodiment, the endoscope apparatus 1 includes the objective optical system 17, the angle of view of which hardly changes even when the focusing lens 26 is moved within the moving range. Therefore, enlargement processing and reduction processing necessary for keeping the display size constant when the angle of view changes are unnecessary. Simple image processing only has to be performed. Note that, in the other embodiments explained below, an endoscope apparatus includes an objective optical system, an angle of view of which hardly changes and has the same effects when the focusing lens 26 is moved within the moving range as with this embodiment.

Through an observation of the diagnosis target region in the state of the high resolving power on the near point side, the surgeon can smoothly perform a diagnosis concerning whether the region is a lesion tissue. When the surgeon ends the diagnosis for the region and continues a screening test for other regions, the surgeon operates the change-over switch SW1.

As shown in step S11, the CPU 36 monitors whether the change-over switch SW1 is operated. When determining that the change-over switch SW1 is not operated (No in step S11), the CPU 36 returns to the processing of the autofocus control in step S7.

On the other hand, when determining that the change-over switch SW1 is operated (Yes in step S11), in step S12, the CPU 36 determines whether an instruction for ending the observation (the examination) by the endoscope 2 is issued. When the instruction for the end is not issued (No in step S12), the CPU 36 returns to the processing in step S2 and performs the autofocus control in the first moving range Ka.

Figure 8:
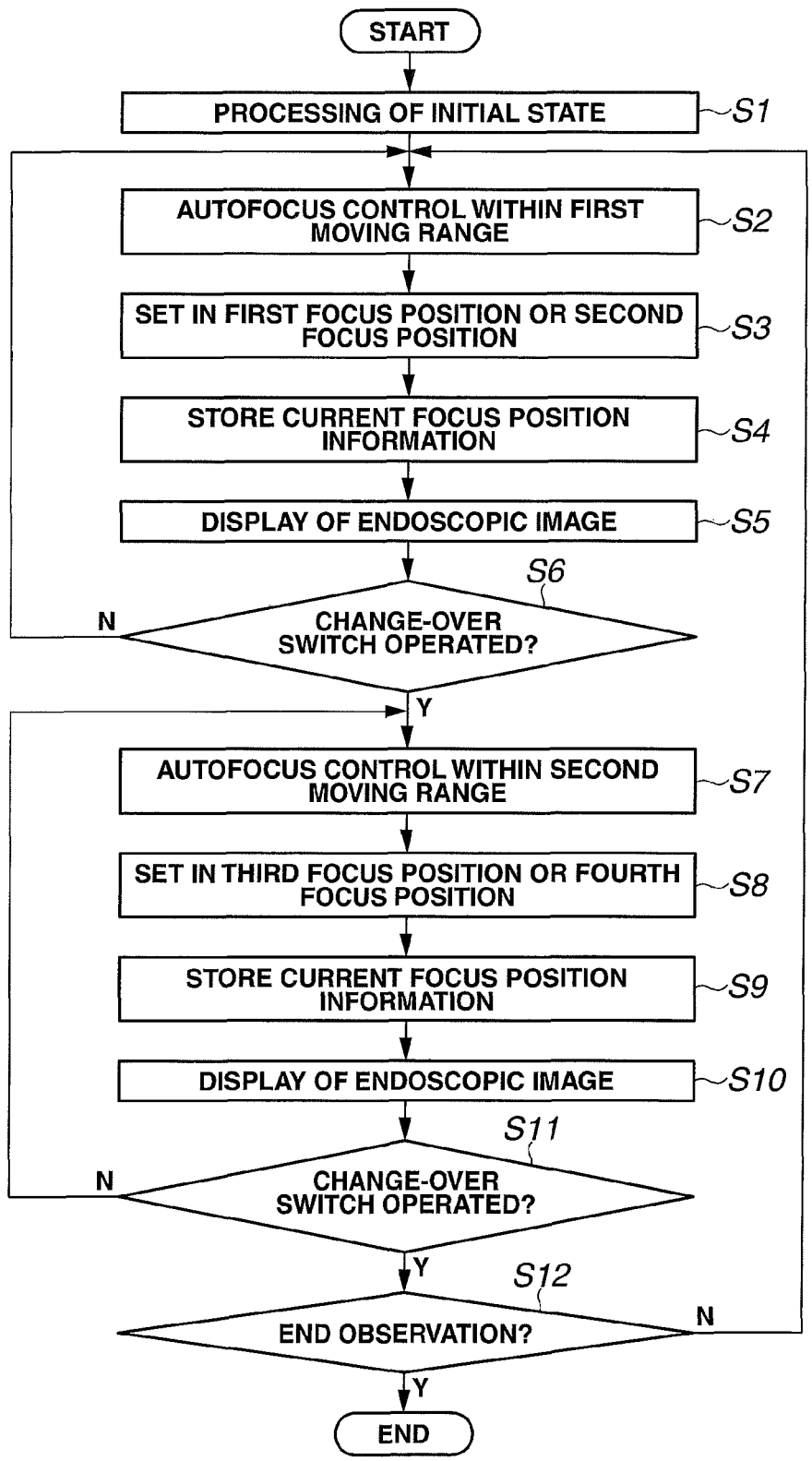
FIG. 8 is a flowchart for explaining a schematic operation in the first embodiment.

On the other hand, when the end is instructed (Yes in step S12), the CPU 36 turns off the power supply of the endoscope apparatus 1 and ends the operation shown in FIG. 8.

According to this embodiment in which the endoscope apparatus 1 operates as explained above, it is possible to improve autofocus speed, reduce a malfunction, and provide an endoscope apparatus that satisfies observation conditions suitable for smoothly performing an examination or an observation by an endoscope on a farthest point side.

More specifically, a movable range of the focusing lens 26 is divided into a plurality of movable ranges and the focusing lens 26 is restricted to move within the divided movable ranges. Therefore, it is possible to set a moving amount smaller than a moving amount set when the focusing lens 26 is not restricted and set the objective optical system 17 in the focused state in a short time.

In this embodiment, the objective optical system 17 is controlled to be auto-focused between the two focus positions within the divided respective moving ranges. Therefore, it is possible to set the objective optical system 17 in the focused state in a shorter time.

A focus region in which the objective optical system 17 can be set in the focused state according to the movement of the focusing lens 26 is limited to one of a plurality of focus regions. Therefore, even in the case of an image pickup condition under which it is difficult to auto-focus the objective optical system 17, for example, even in the case of an image pickup condition in which a contrast change in an endoscopic image is small or an image pickup state in which noise tends to affect because of use of an electric knife or the like, it is possible to effectively prevent a malfunction in which the objective optical system 17 is defocused in a position substantially different from a position where the objective optical system 17 should be focused.

In the farthest point side, the image pickup unit 19 provided at the distal end portion 11 can satisfy observation conditions that the image pickup unit 19 has resolving power equal to or higher than 35 μm and has width of depth of field equal to or larger than 5 mm in a focus position at a distance equal to or smaller than 15 mm to an object. Therefore, it is possible to smoothly perform an examination or an observation by the endoscope 2.

As explained above, with the endoscope apparatus 1 according to this embodiment, the surgeon can smoothly perform an examination or an observation using the endoscope 2.

Second Embodiment

Next, a second embodiment of the present invention is explained. An endoscope apparatus according to this embodiment is different from the endoscope apparatus 1 according to the first embodiment shown in FIG. 1 in an objective optical system and a CCD. In this embodiment, an objective optical system 17B shown in FIGS. 9(A) and 9(B) is adopted and a CCD 18B having a pixel pitch P of 2.3 μm is adopted.

FIGS. 9(A) and 9(B) respectively show sectional views of the objective optical system 17B in states in which the objective optical system 17B is set in the first focus position and a fifth focus position. In the objective optical system 17B, the front group G1 is configured by the concave lens L1, a parallel flat plate L2, and the convex lens L3 (26). The rear group G2 is configured by a diaphragm, the convex lens L4, the cemented lens of the convex lens L5 and the concave lens L6, and a parallel flat plate L7. Flat optical elements I1 and I2 are arranged behind the parallel flat plate L7. The CCD 18B including the mosaic color filter 18a is arranged on a rear surface of the optical element 12.

Figure 10:
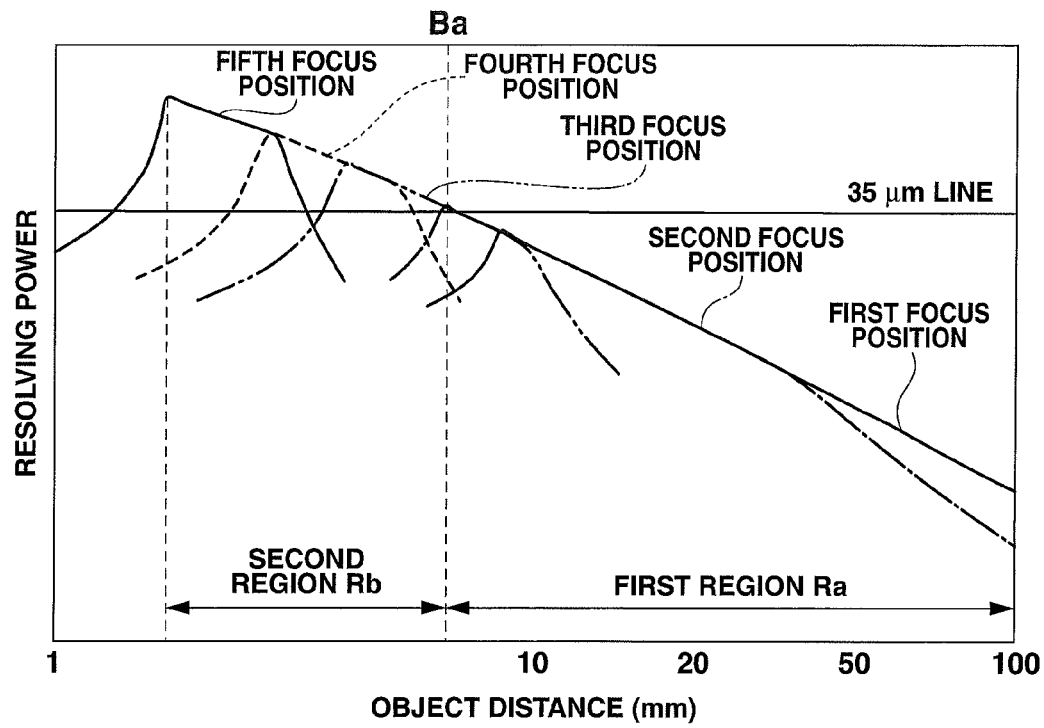
FIG. 10 is a diagram showing a relation between an object distance and resolving power in states in which the objective optical system is set in respective focus positions in the second embodiment.

Other hardware components are the same as the components shown in FIG. 1. The components are explained using the same reference numerals and signs. In this embodiment, concerning focus positions where the objective optical system 17B is set in a focused state, as shown in FIG. 10, the objective optical system 17B is set in the first focus position or the second focus position in the first region Ra and set in the third to fifth focus positions in the second region Rb.

Therefore, the memory 38 stores setting information necessary for positioning the focusing lens 26 in order to set the objective optical system 17B in the first to fifth focus positions.

Numerical value data in this embodiment is shown below.

| Numerical value data in the second embodiment | | | | |
|---|---|---|---|---|
| Surface number | Curvature radius | Surface interval | Refractive index | Abbe number |
| Object surface | ∞ | D0 | | |
| 1 | ∞ | 0.4 | 1.88815 | 40.76 |
| 2 | 1.1238 | 0.76 | | |
| 3 | ∞ | 0.62 | 1.51965 | 75 |
| 4 | ∞ | D4 | | |
| 5 | 1.2768 | 0.55 | 1.88815 | 40.76 |
| 6 | 1.4194 | D6 | | |
| 7 (Diaphragm) | ∞ | 0.11 | | |
| 8 | 2.7182 | 1.09 | 1.48915 | 70.23 |
| 9 | −2.7182 | 1.17 | | |
| 10 | 4.7991 | 1.49 | 1.77621 | 49.6 |
| 11 | −2.0966 | 0.34 | 1.93429 | 18.9 |
| 12 | −8.0131 | 0.18 | | |
| 13 | ∞ | 0.41 | 1.52513 | 58.5 |
| 14 | ∞ | 0.6 | | |
| 15 | ∞ | 0.95 | 1.51825 | 64.14 |
| 16 | ∞ | 0.75 | 1.61379 | 50.2 |
| (Image surface) | ∞ | | | |

| | First focus position | Second focus position | Third focus position | Fourth focus position | Fifth focus position |
|---|---|---|---|---|---|
| D0 | 18 | 11 | 5.5 | 3.54 | 2.12 |
| D4 | 0.14 | 0.22 | 0.39 | 0.54 | 0.74 |
| D6 | 0.68 | 0.6 | 0.43 | 0.28 | 0.08 |
| Width of depth of field (mm) | 8.4 to 100 or larger | 6.3 to 35 | 3.82 to 9.4 | 2.63 to 5.16 | 1.66 to 2.85 |
| Angle of view (°) | 133.3 | 132.3 | 130.5 | 129.6 | 129.4 |
| Pitch P | 2.3 μm | | | | |
| IH | 1.346 | | | | |
| IH/P | 585.2 | | | | |
| f | 1.355 | | | | |
| IH/f | 0.911 | | | | |

-continued

Numerical value data in the second embodiment

| | |
|---|---|
| Resolution | 33.5 μm |
| | (At time |
| | of 6.3 mm) |
| $f_{focus}$ | 5.085 |
| $f_{focus}/f$ | 3.44 |

In this embodiment, a zone in a focused state on a near point side is enlarged to be larger than a zone in the first embodiment. That is, when the objective optical system 17B is set in the fifth focus position, it is possible to examine or observe a diseased part or the like in detail in close proximity thereto at width of depth of field of 1.66 mm to 2.85 mm. Besides, this embodiment has effects substantially the same as the effects in the first embodiment.

As a modification of this embodiment, the second region Rb on the near point side may be covered by two moving ranges. More specifically, the second moving range Kb that covers the second region Rb in the case of this embodiment is divided into a moving range Kb1 in which width of depth of field is equal to or larger than 2.5 mm and a moving range Kb2 in which depth range is smaller than 2.5 mm. The second region Rb is not limited to be divided at a value of 2.5 mm of the width of depth of field and may be divided at a value of about 2 mm to 3 mm.

Figure 11:
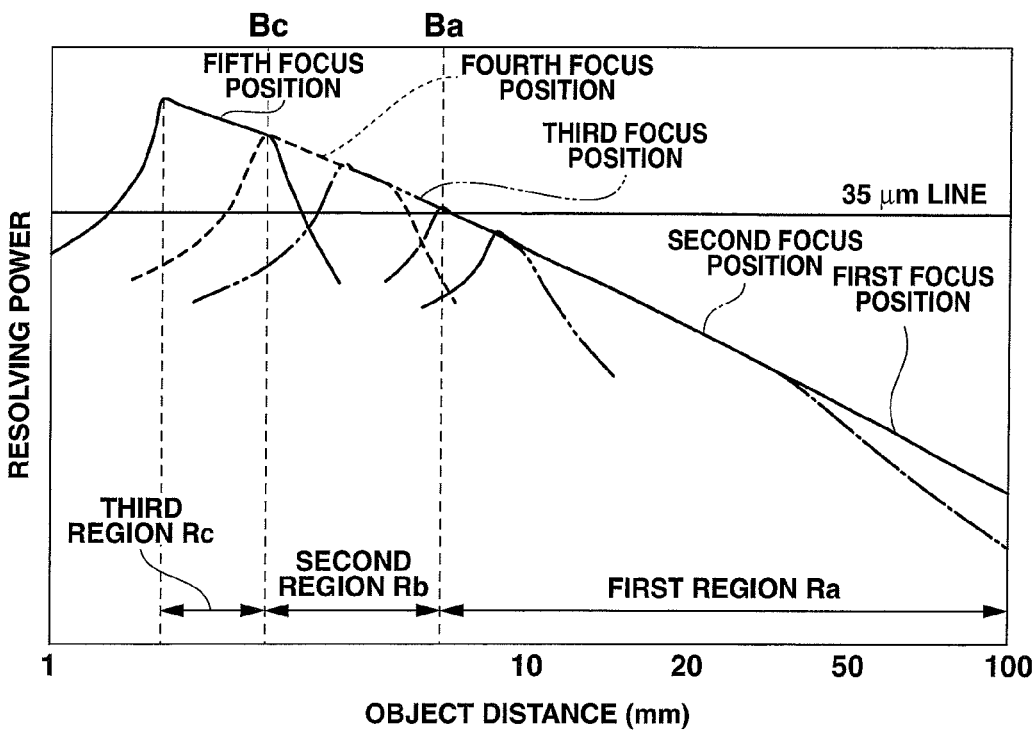
FIG. 11 is a diagram showing a relation between an object distance and resolving power in states in which the objective optical system is set in respective focus positions when the number of moving ranges is set to three in the second embodiment.

A boundary of an object distance in the second moving range Kb divided into the moving ranges Kb1 and Kb2 in this case is as indicated by a dotted line Bc in FIG. 11. The second region Rb is divided into the second region Rb and a third region Rc by the boundary Bc. When the second region Rb is divided in this way, one focus position is set in the third region Rc. Note that the objective optical system 17B may be configured to be able to be further set in a plurality of focus positions.

Third Embodiment

Next, a third embodiment of the present invention is explained. An endoscope apparatus according to this embodiment is different from the endoscope apparatus 1 according to the first embodiment shown in FIG. 1 in an objective optical system and a CCD. In this embodiment, an objective optical system 17C shown in FIGS. 12(A) and 12(B) is adopted and a CCD 18C having a pixel pitch P of 1.4 μm is adopted.

FIGS. 12(A) and 12(B) respectively show sectional views of the objective optical system 17C in states in which the objective optical system 17C is set in the first focus position and the fourth focus position.

In the objective optical system 17C, the front group G1 is configured by the concave lens L1, the concave lens L2, and the convex lens L3 (26). The rear group G2 is configured by a diaphragm, the convex lens L4, the cemented lens of the convex lens L5 and the concave lens L6, and parallel flat plates L7 and L8. The flat optical elements I1 and I2 are arranged behind the parallel flat plate L8. The CCD 18C including the mosaic color filter 18a is arranged on the rear surface of the optical element 12. Other hardware components are the same as the components shown in FIG. 1. Numerical value data in this embodiment is shown below.

Numerical value data in the third embodiment

| Surface number | Curvature radius | Surface interval | Refractive index | Abbe number |
|---|---|---|---|---|
| Object surface | ∞ | D0 | | |
| 1 | ∞ | 0.4 | 1.81991 | 44.36 |
| 2 | 1.2646 | 1.18 | | |
| 3 | −1.7487 | 0.52 | 1.88815 | 40.76 |
| 4 | −1.8479 | D4 | | |
| 5 | 2.352 | 0.815 | 1.50349 | 56.42 |
| 6 | 3.0877 | D6 | | |
| 7 (Diaphragm) | ∞ | 0.07 | | |
| 8 | 3.4714 | 1.22 | 1.48915 | 70.23 |
| 9 | −3.1907 | 0.87 | | |
| 10 | 3.2151 | 1.199 | 1.48915 | 70.23 |
| 11 | −1.7375 | 0.3 | 1.93429 | 18.9 |
| 12 | −3.7434 | 0.095 | | |
| 13 | ∞ | 0.246 | 1.51564 | 75.01 |
| 14 | ∞ | 0.243 | | |
| 15 | ∞ | 0.318 | 1.52513 | 58.5 |
| 16 | ∞ | 0.71 | | |
| 17 | ∞ | 0.79 | 1.51825 | 64.14 |
| 18 | ∞ | 0.52 | 1.50801 | 60 |
| (Image surface) | ∞ | | | |

| | First focus position | Second focus position | Third focus position | Fourth focus position |
|---|---|---|---|---|
| D0 | 28 | 14.7 | 9.45 | 6.25 |
| D4 | 0.25 | 0.5 | 0.75 | 1.05 |
| D6 | 0.843 | 0.593 | 0.343 | 0.043 |
| Width of depth of field (mm) | 15.3 to 100 or larger | 10 to 26 | 7.1 to 13.7 | 5 to 8.15 |
| Angle of view (°) | 128.9 | 129 | 129.5 | 130.6 |
| Pitch P | 1.4 μm | | | |
| IH | 1.284 | | | |
| IH/P | 917 | | | |
| f | 1.365 | | | |
| IH/f | 0.941 | | | |
| Resolution | 34.1 μm (At time of 10 mm) | | | |
| $f_{focus}$ | 14.3 | | | |
| $f_{focus}/f$ | 10.48 | | | |

Figure 13:
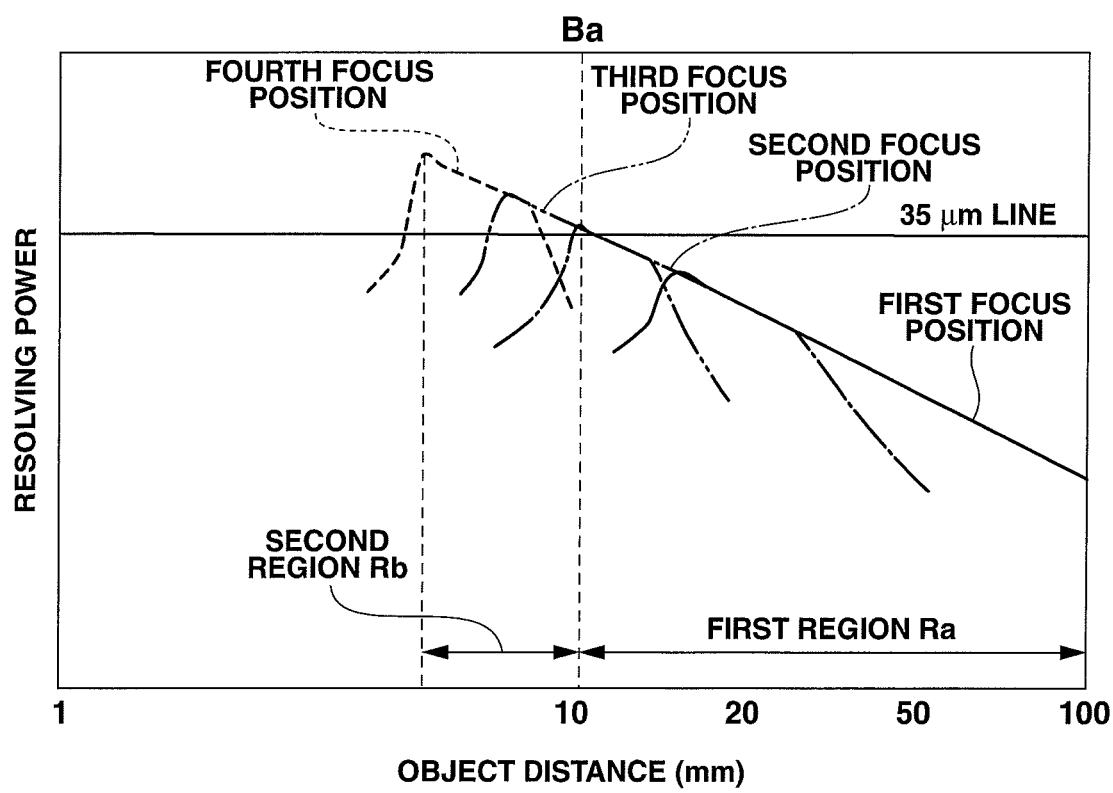
FIG. 13 is a diagram showing a relation between an object distance and resolving power in states in which the objective optical system is set in respective focus positions in the third embodiment.

In this embodiment, the objective optical system 17C in this embodiment is similar to a configuration in which the parallel flat plates L7 and L8 are arranged between the cemented lens and the optical element I1 in the objective optical system 17 in the first embodiment. A characteristic of resolving power with respect to an object distance in this embodiment is as shown in FIG. 13. The characteristic is similar to the characteristic in the first embodiment.

Effects in this embodiment are substantially the same as the effects in the first embodiment.

Fourth Embodiment

Next, a fourth embodiment of the present invention is explained. An endoscope apparatus according to this embodiment is different from the endoscope apparatus 1 according to the first embodiment shown in FIG. 1 in an objective optical system and a CCD. In this embodiment, an objective optical system 17D shown in FIGS. 14(A) and 14(B) is adopted and a CCD 18D having a pixel pitch P of 1.6 μm is adopted.

FIGS. 14(A) and 14(B) respectively show sectional views of the objective optical system 17D in states in which the objective optical system 17D is set in the first focus position and a sixth focus position. In the objective optical system 17D, the front group G1 is configured by the concave lens L1, the concave lens L2, and the convex lens L3 (26). The rear group G2 is configured by a diaphragm, the convex lens L4, and the cemented lens of the convex lens L5 and the concave lens L6. The flat optical elements I1 and I2 are arranged behind the cemented lens. The CCD 18D including the mosaic color filter 18a is arranged on the rear surface of the optical element 12.

Other hardware components are the same as the components shown in FIG. 1.

Figure 15:
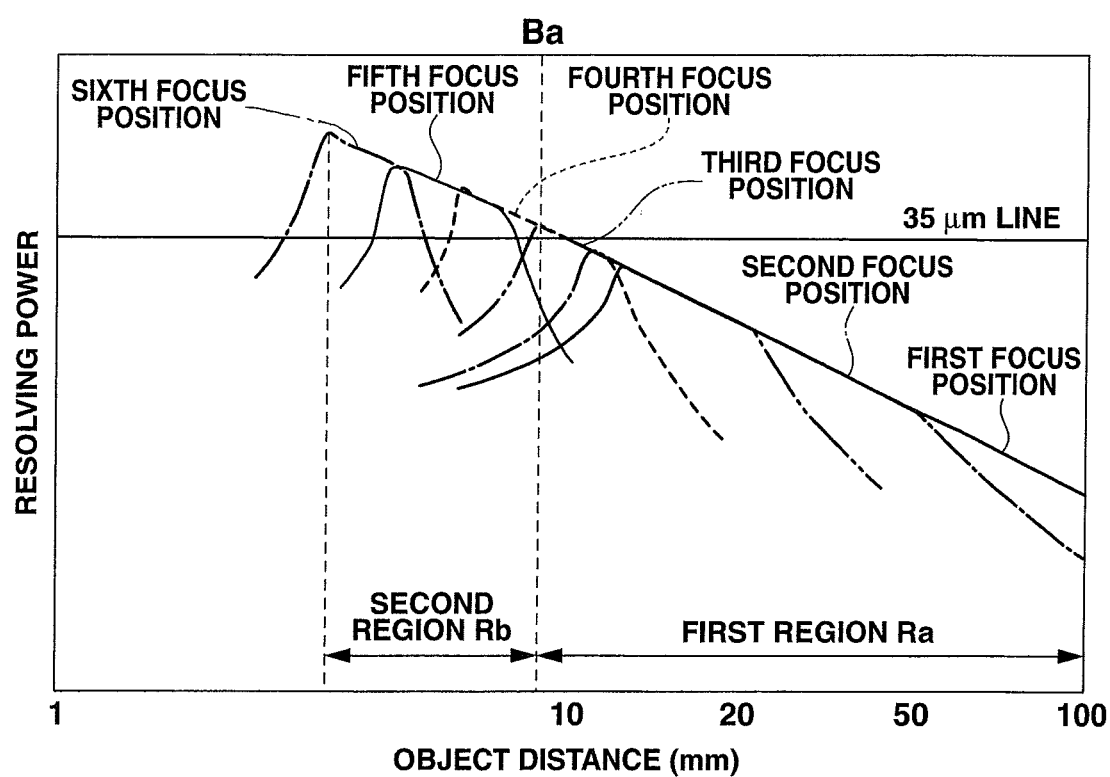
FIG. 15 is a diagram showing a relation between an object distance and resolving power in states in which the objective optical system is set in respective focus positions in the fourth embodiment.

In this embodiment, concerning focus positions where the objective optical system 17D is set in a focused state, as shown in FIG. 15, the objective optical system 17D is set in the first to third focus positions in the first region Ra and set in the fourth to sixth focus positions in the second region Rb.

Therefore, the memory 38 stores setting information necessary for positioning the focusing lens 26 in order to set the objective optical system 17D in the first to sixth focus positions.

Numerical value data in this embodiment is shown below.

| Numerical value data in the fourth embodiment | | | | |
|---|---|---|---|---|
| Surface number | Curvature radius | Surface interval | Refractive index | Abbe number |
| Object surface | ∞ | D0 | | |
| 1 | ∞ | 0.4 | 1.88815 | 40.76 |
| 2 | 1.4202 | 0.38 | | |
| 3 | 5.8125 | 0.6 | 1.48972 | 70.17 |
| 4 | 1.4609 | D4 | | |
| 5 | 1.7468 | 0.49 | 1.52545 | 50.5 |
| 6 | 4.4207 | D6 | | |
| 7 (Diaphragm) | ∞ | 0.05 | | |
| 8 | 4.2705 | 2.44 | 1.88885 | 37.24 |
| 9 | −3.7495 | 0.15 | | |
| 10 | 6.4642 | 1.2 | 1.63801 | 59.32 |
| 11 | −1.5 | 0.3 | 1.9343 | 18.9 |
| 12 | −4.4713 | 1.012 | | |
| 13 | ∞ | 1.88 | 1.51825 | 64.14 |
| 14 | ∞ | 1.0 | 1.50801 | 60 |
| (Image surface) | ∞ | | | |

| | First focus | Second focus | Third focus | Fourth focus | Fifth focus | Sixth focus |
|---|---|---|---|---|---|---|
| D0 | 22.7 | 17.8 | 12.2 | 8.05 | 5.52 | 3.72 |
| D4 | 0.247 | 0.267 | 0.307 | 0.367 | 0.437 | 0.527 |
| D6 | 0.872 | 0.852 | 0.812 | 0.752 | 0.682 | 0.592 |
| Width of depth of field (mm) | 12.5 to 100 or larger | 10.7 to 46.5 | 8.22 to 22.2 | 5.96 to 11.8 | 4.35 to 7.32 | 3.06 to 4.61 |
| Angle of view (°) | 130.4 | 130.3 | 130.3 | 130.3 | 130.5 | 130.9 |
| Assumed pitch P | | 1.6 μm | | | | |
| IH | | 1.29 | | | | |
| IH/P | | 806 | | | | |
| f | | 1.345 | | | | |
| IH/f | | 0.96 | | | | |
| Resolution | | 32.7 μm (At time of 8.22 mm) | | | | |
| $f_{focus}$ | | 5.17 | | | | |
| $f_{focus}/f$ | | 3.84 | | | | |

In this embodiment, three focus zones are set on each of a near point side and a far point side. Besides, this embodiment has effects substantially the same as the effects in the first embodiment.

Fifth Embodiment

Figure 16:
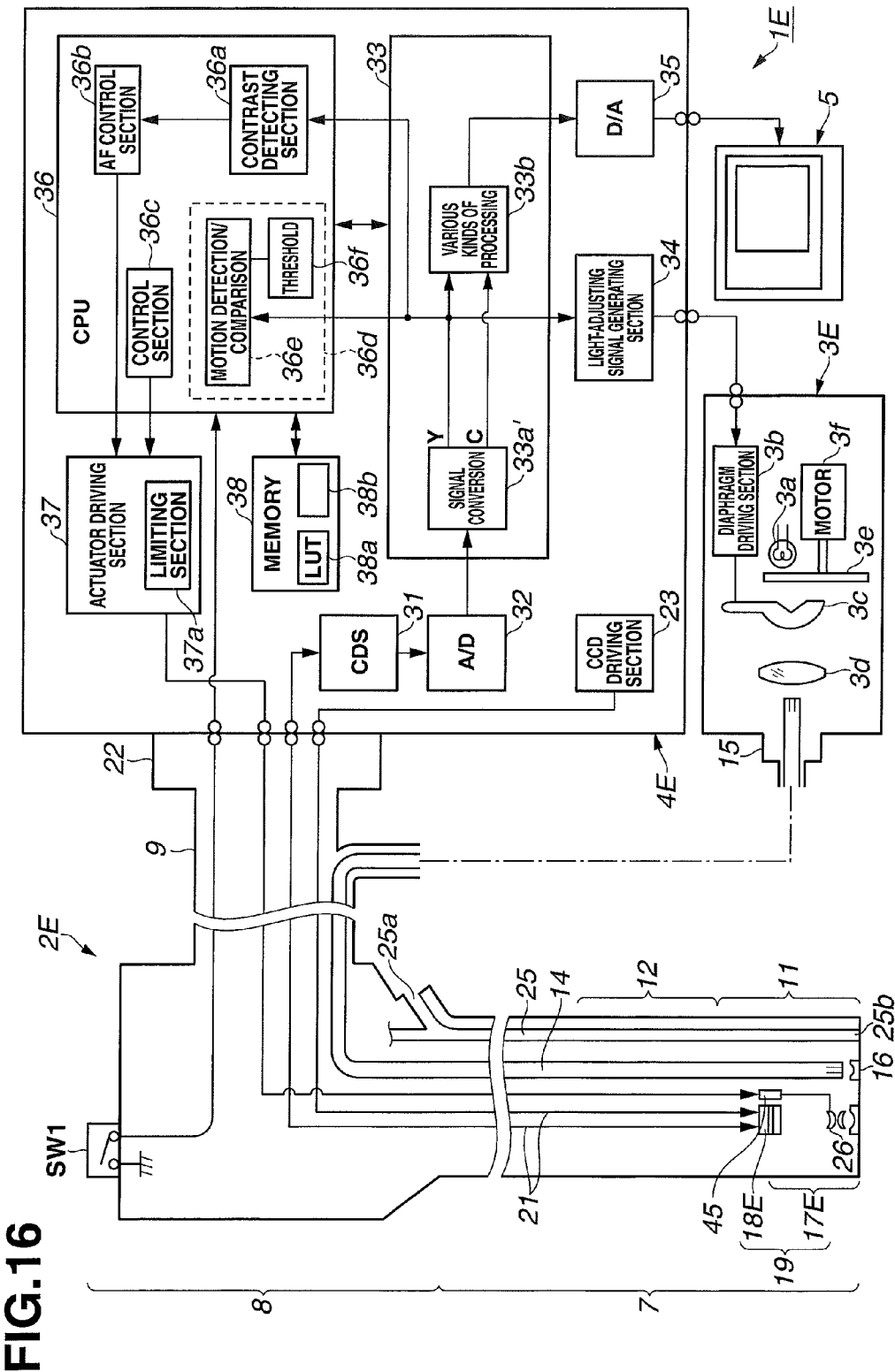
FIG. 16 is a diagram showing an overall configuration of an endoscope apparatus according to a fifth embodiment of the present invention.

Next, a fifth embodiment of the present invention is explained. FIG. 16 shows an endoscope apparatus 1E according to this embodiment. The endoscope apparatus 1E is different from the endoscope apparatus 1 according to the first embodiment shown in FIG. 1 in an objective optical system and a CCD. A light source device 3E and an image processing device 4E slightly different from the light source device 3 and the image processing device 4 shown in FIG. 1 are adopted. In this embodiment, an objective optical system 17E shown in FIGS. 17(A) and 17(B) is adopted and a monochrome CCD 18E having a pixel pitch P of 2.5 μm is adopted.

FIGS. 17(A) and 17(B) respectively show sectional views of the objective optical system 17E in states in which the objective optical system 17E is set in the first focus position and the sixth focus position. In the objective optical system 17E, the front group G1 is configured by the concave lens L1, the concave lens L2, and the convex lens L3 (26). The rear group G2 is configured by a diaphragm, the convex lens L4, and the cemented lens of the convex lens L5 and the concave lens L6. The flat optical elements I1 and I2 are arranged behind the cemented lens. The CCD 18E is arranged on the rear surface of the optical element 12.

In the light source device 3E, a rotating filter 3e is arranged in an optical path between the lamp 3a and the diaphragm 3c in the light source device 3 shown in FIG. 1. The rotating filter 3e is rotated by a motor 3f to supply frame-sequential R, G, and B illumination lights to the light guide 14.

An image is picked up by the monochrome CCD 18E. The monochrome CCD 18E generates frame-sequential R, G, and B luminance signals under the frame-sequential R, G, and B illumination lights.

The image processing device 4E includes a signal converting circuit 33a' configured to perform signal conversion slightly different from the signal conversion by the signal converting circuit 33a in the image processing device 4 shown in FIG. 1.

The signal converting circuit 33a' temporarily stores frame-sequentially picked-up R, G, and B image signals in a memory, simultaneously reads out the R, G, and B image signals to generate synchronized R, G, and B image signals, and converts the synchronized R, G, and B image signals into the luminance signal Y and the color signal C with a matrix circuit.

Other signal processing by the image processing device 4E is the same as the signal processing by the image processing device 4 shown in FIG. 1. A configuration of the endoscope apparatus 1E is a configuration similar to the configuration in the first embodiment except that the monochrome CCD 18E is adopted.

Figure 18:
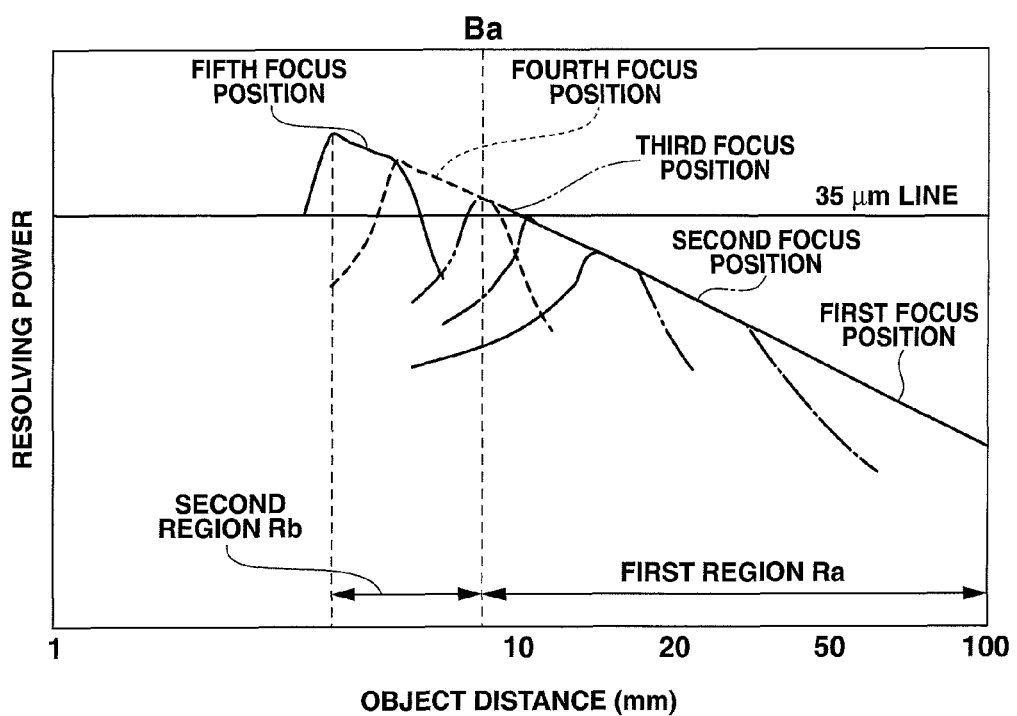
FIG. 18 is a diagram showing a relation between an object distance and resolving power in states in which the objective optical system is set in respective focus positions in the fifth embodiment.

A characteristic of resolving power in this embodiment is shown in FIG. 18. Numerical value data in this embodiment is as shown below.

| Numerical value data in the fifth embodiment | | | | |
|---|---|---|---|---|
| Surface number | Curvature radius | Surface interval | Refractive index | Abbe number |
| Object surface | ∞ | D0 | | |
| 1 | ∞ | 0.4 | 1.88815 | 40.76 |
| 2 | 1.4202 | 0.38 | | |
| 3 | 5.8125 | 0.6 | 1.48972 | 70.17 |
| 4 | 1.4609 | D4 | | |
| 5 | 1.7468 | 0.49 | 1.52545 | 50.5 |
| 6 | 4.4207 | D6 | | |
| 7 (Diaphragm) | ∞ | 0.05 | | |
| 8 | 4.2705 | 2.44 | 1.88885 | 37.24 |
| 9 | −3.7495 | 0.15 | | |
| 10 | 6.4642 | 1.2 | 1.63801 | 59.32 |
| 11 | −1.5 | 0.3 | 1.9343 | 18.9 |
| 12 | −4.4713 | 1.012 | | |

-continued

Numerical value data in the fifth embodiment

| 13 | ∞ | 1.88 | 1.51825 | 64.14 |
|---|---|---|---|---|
| 14 | ∞ | 1.0 | 1.50801 | 60 |
| (Image surface) | ∞ | | | |

| | First focus position | Second focus position | Third focus position | Fourth focus position | Fifth focus position |
|---|---|---|---|---|---|
| D0 | 22.7 | 16 | 11.4 | 6.84 | 4.65 |
| D4 | 0.27 | 0.32 | 0.37 | 0.47 | 0.57 |
| D6 | 0.95 | 0.9 | 0.85 | 0.75 | 0.65 |
| Depth (mm) | 14.3 to 100 or larger | 10.5 to 31.7 | 8.1 to 18 | 5.37 to 9.17 | 3.83 to 5.81 |
| Angle of view (°) | 128.1 | 128.1 | 128.1 | 28.2 | 128.6 |
| Pitch P | 2.5 μm | | | | |
| IH | 1.29 | | | | |
| IH/P | 554 | | | | |
| f | 1.345 | | | | |
| IH/f | 0.935 | | | | |
| Resolution | 30.75 μm (At time of 8.1 mm) | | | | |
| $f_{focus}$ | 6.294 | | | | |
| $f_{focus}/f$ | 4.25 | | | | |

The endoscope apparatus 1E according to this embodiment has a configuration and a characteristic explained below.

The endoscope apparatus 1E includes an endoscope 2E inserted into a tube cavity, an objective optical system 17E mounted at a distal end portion 19 of the endoscope 2E and configured to form an image of an object in the tube cavity, the objective optical system 17E including the focusing lens 26 movable in an optical axis direction and satisfying conditional expressions (1) and (2) explained above, a CCD 18E functioning as a monochrome solid-state image pickup device configured to pick up the image formed by the objective optical system 17E, the CCD 18E satisfying a conditional expression (4) below and generating a luminance signal for each pixel, a focus adjusting mechanism 27 configured to move the focusing lens 26 and automatically adjust the objective optical system 17E to a focus position in a focused state, a change-over switch SW1 functioning as moving range switching means for performing switching of a moving range of the focusing lens 26, a limiting section 37a functioning as moving range limiting means for limiting the moving range using a signal in association with the switching by the moving range switching means, and a memory 38 configured to store information for adjusting the objective optical system 17E to a plurality of focus positions, where the objective optical system 17E is in the focused state, with the focus adjusting mechanism 27 in the moving range limited by the moving range limiting means. When the objective optical system 17E is automatically adjusted to a focus position by the focus adjusting mechanism 27 according to the information stored in the setting information storing means in a moving range on a farthest point side limited by the moving range limiting means, resolving power on the optical axis of the objective optical system 17E has resolving power equal to or larger than 35 μm in a focus position where a distance between the objective optical system 17E and the object is equal to or smaller than 15 mm. When a range in which MTF of a spatial frequency 1/(2×P) on the optical axis of the objective optical system 17E is equal to or higher than 10% is defined as width of depth of field, the objective optical system 17E has width of depth of field equal to or larger than 5 mm, $$360 < IH/P < 800 \quad (4)$$

where, IH represents a distance from a center in an image pickup region of a solid-state image pickup device to a most distant position and P represents a pixel pitch of the solid-state image pickup device.

In the other embodiments explained below, the conditional expressions (1), (2), and (4) are satisfied. In this embodiment, the conditional expression (4) 360<IH/P<800 is different from the conditional expression (3) in the embodiment including the color separation filter.

In the operation of the endoscope apparatus 1E according to this embodiment, the monochrome CCD 18E is used as the solid-state image pickup device. Therefore, the endoscope apparatus 1E has effects explained below in which width of depth of field is improved from the width of depth of field of the CCD 18 for color image pickup.

That is, in the farthest point side, the image pickup unit 19 provided at the distal end portion 11 can satisfy predetermined observation conditions that the image pickup unit 19 has resolving power equal to or higher than 35 μm and has width of depth of field equal to or larger than 5 mm in a focus position at a distance equal to or smaller than 15 mm to an object. Therefore, it is possible to smoothly perform an examination or an observation by the endoscope 2.

However, in this embodiment, the objective optical system 17E is configured to be set in three focus positions in the first region Ra on the far point side and set in two focus positions in the second region Rb on the near point side.

As effects of this embodiment, an observation can be performed at further improved width of depth of field than the case of, for example, the CCD 18 for color image pickup as explained above in the moving range on the far point side. Besides, substantially the same as in the first embodiment, it is possible to improve autofocus speed, reduce a malfunction, and provide an endoscope apparatus that satisfies observation conditions suitable for smoothly performing an examination or an observation by an endoscope on a farthest point side.

Sixth Embodiment

Next, a sixth embodiment of the present invention is explained. An endoscope apparatus according to this embodiment adopts an objective optical system 17F and a CCD 18F different from the objective optical system 17E and the CCD 18E of the endoscope apparatus 1E according to the fifth embodiment shown in FIG. 16. In this embodiment, the objective optical system 17F shown in FIGS. 19(A) and 19(B) is adopted and the CCD 18F having the pixel pitch P of 2.5 μm is adopted.

FIGS. 19(A) and 19(B) respectively show sectional views of the objective optical system 17F in states in which the objective optical system 17F is set in the first focus position and the fifth focus position. In the objective optical system 17F, the front group G1 is configured by the concave lens L1, the concave lens L2, and the convex lens L3 (26). The rear group G2 is configured by a diaphragm, the convex lens L4, and the cemented lens of the convex lens L5 and the concave lens L6. The flat optical element I1 is arranged behind the cemented lens. The CCD 18F is arranged on the rear surface of the optical element I1.

Figure 20:
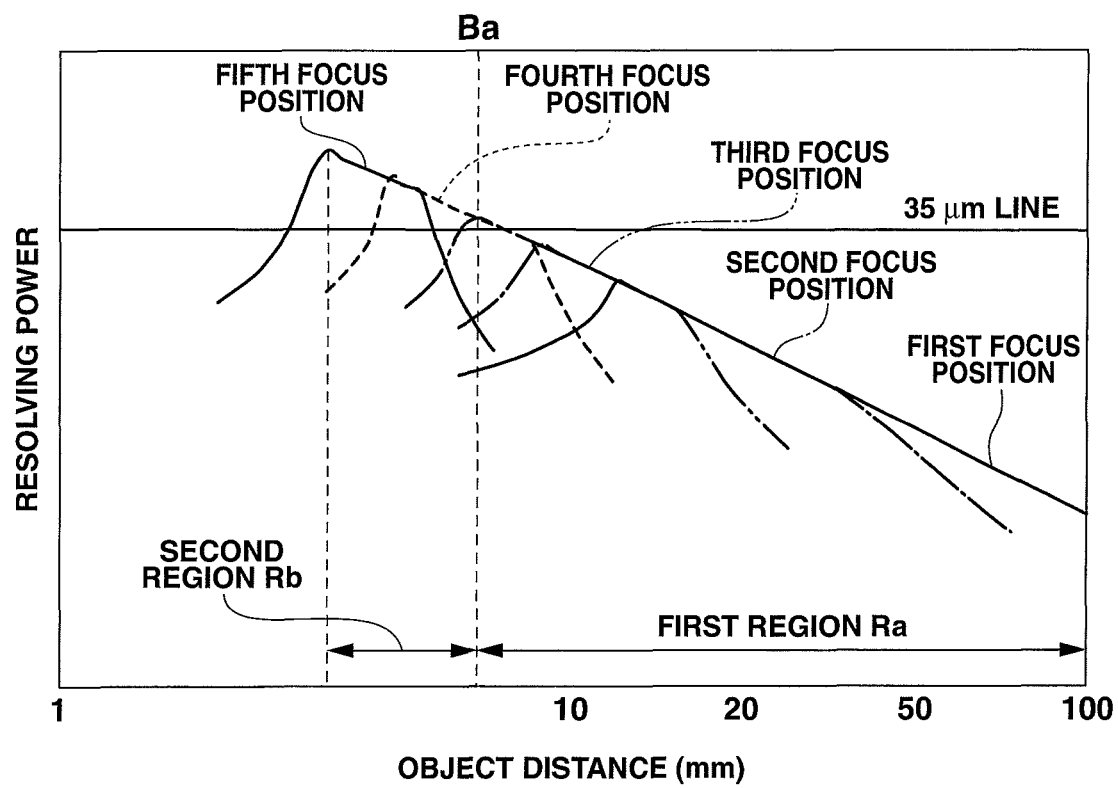
FIG. 20 is a diagram showing a relation between an object distance and resolving power in states in which the objective optical system is set in respective focus positions in the sixth embodiment.

Other hardware components are the same as the components shown in FIG. 16. A characteristic of resolving power in this embodiment is shown in FIG. 20. Numerical value data in this embodiment is shown below.

Numerical value data in the sixth embodiment

| Surface number | Curvature radius | Surface interval | Refractive index | Abbe number |
|---|---|---|---|---|
| Object surface | ∞ | D0 | | |
| 1 | ∞ | 0.32 | 1.88815 | 40.76 |
| 2 | 0.9624 | 0.47 | | |
| 3 | −5.0462 | 0.48 | 1.88151 | 41.14 |
| 4 | −31.2269 | D4 | | |
| 5 | 2.0961 | 1.03 | 1.50363 | 60.42 |
| 6 | 17.7264 | D6 | | |
| 7 (Diaphragm) | ∞ | 0.04 | | |
| 8 | 2.2826 | 1.26 | 1.64065 | 29.99 |
| 9 | −4.7152 | 0.12 | | |
| 10 | 4.0928 | 0.96 | 1.68137 | 56.93 |
| 11 | −1.0154 | 0.24 | 1.92601 | 20.84 |
| 12 | −4.0318 | 1.16 | | |
| 13 | ∞ | 1.92 | 1.51825 | 64.14 |
| (Image surface) | ∞ | | | |

| | First focus position | Second focus position | Third focus position | Fourth focus position | Fifth focus position |
|---|---|---|---|---|---|
| D0 | 26.5 | 13.8 | 9.1 | 5.75 | 3.86 |
| D4 | 0.2 | 0.24 | 0.28 | 0.34 | 0.41 |
| D6 | 0.7 | 0.66 | 0.62 | 0.56 | 0.49 |
| Width of depth of field (mm) | 11.9 to 100 or larger | 8.2 to 36.8 | 6.13 to 16.1 | 4.31 to 8.3 | 3.07 to 5.03 |
| Angle of view (°) | 124 | 123.9 | 123.9 | 124.1 | 124.4 |
| Pitch P | 2.5 μm | | | | |
| IH | 0.992 | | | | |
| IH/P | 396.8 | | | | |
| f | 1.086 | | | | |
| IH/f | 0.914 | | | | |
| Resolution | 31.7 μm (At time of 6.13 mm) | | | | |
| $f_{focus}$ | 6.294 | | | | |
| $f_{focus}/f$ | 4.25 | | | | |

This embodiment has effects substantially the same as the effects in the fifth embodiment.

Seventh Embodiment

A seventh embodiment of the present invention is explained. An endoscope apparatus according to this embodiment adopts an objective optical system 17G and a CCD 18G different from the objective optical system 17E and the CCD 18E of the endoscope apparatus 1E according to the fifth embodiment shown in FIG. 16.

In this embodiment, the objective optical system 17G shown in FIGS. 21(A) and 21(B) is adopted and the CCD 18G having the pixel pitch P of 1.8 μm is adopted.

FIGS. 21(A) and 21(B) respectively show sectional views of the objective optical system 17G in states in which the objective optical system 17G is set in the first focus position and the sixth focus position. In the objective optical system 17G, the front group G1 is configured by the concave lens L1, the concave lens L2, and the convex lens L3 (26). The rear group G2 is configured by a diaphragm, the convex lens L4, and the cemented lens of the convex lens L5 and the concave lens L6. The flat optical element I1 is arranged behind the cemented lens. The CCD 18G is arranged on the rear surface of the optical element I1.

Figure 22:
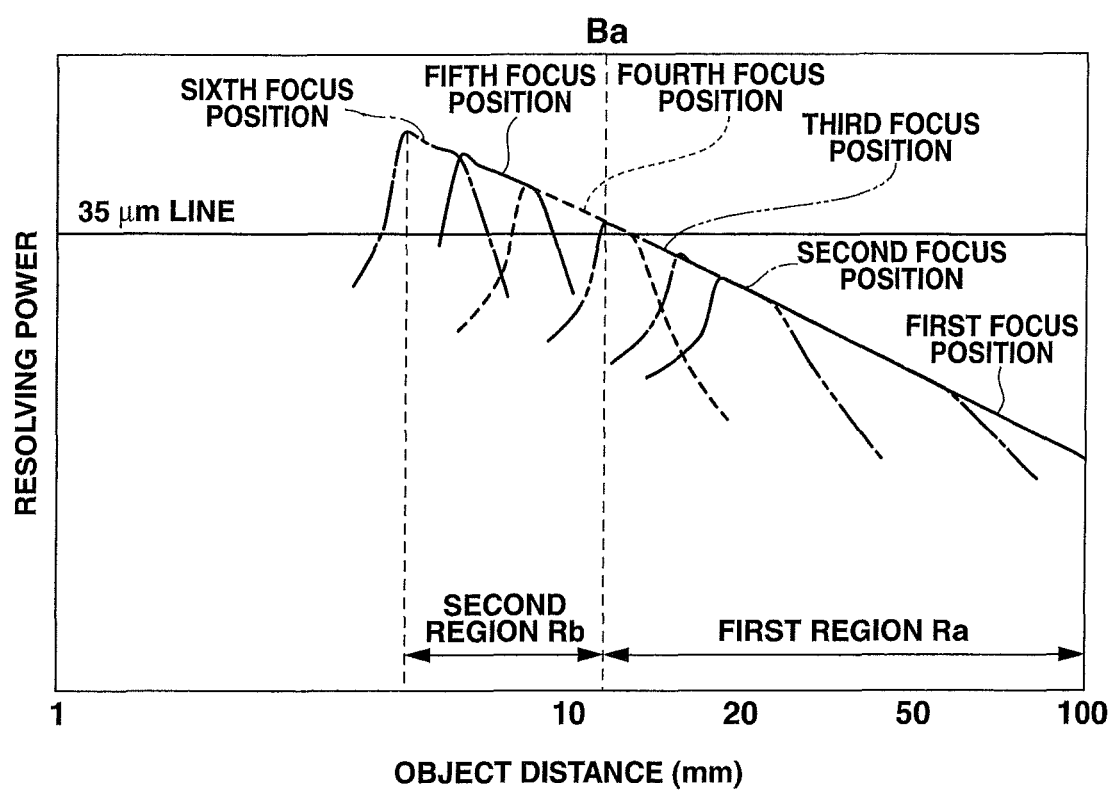
FIG. 22 is a diagram showing a relation between an object distance and resolving power in states in which the objective optical system is set in respective focus positions in the seventh embodiment.

Other hardware components are the same as the components shown in FIG. 16. A characteristic of resolving power in this embodiment is shown in FIG. 22. Numerical value data in this embodiment is shown below.

Numerical value data in the seventh embodiment

| Surface number | Curvature radius | Surface interval | Refractive index | Abbe number |
|---|---|---|---|---|
| Object surface | ∞ | D0 | | |
| 1 | ∞ | 0.4 | 1.88815 | 40.76 |
| 2 | 1.203 | 0.59 | | |
| 3 | −6.3078 | 0.6 | 1.88151 | 41.14 |
| 4 | −39.0336 | D4 | | |
| 5 | 2.6201 | 1.29 | 1.50363 | 60.42 |
| 6 | 22.1581 | D6 | | |
| 7 (Diaphragm) | ∞ | 0.05 | | |
| 8 | 2.8532 | 1.57 | 1.64065 | 29.99 |
| 9 | −5.8939 | 0.15 | | |
| 10 | 5.116 | 1.2 | 1.68137 | 56.93 |
| 11 | −1.2692 | 0.3 | 1.92601 | 20.84 |
| 12 | −5.0398 | 1.378 | | |
| 13 | ∞ | 2.5 | 1.51825 | 64.14 |
| (Image surface) | ∞ | | | |

| | First focus position | Second focus | Third focus | Fourth focus | Fifth focus | Sixth focus |
|---|---|---|---|---|---|---|
| D0 | 33.7 | 24.5 | 15.6 | 9.78 | 6.9 | 5.2 |
| D4 | 0.25 | 0.27 | 0.31 | 0.37 | 0.43 | 0.49 |
| D6 | 0.87 | 0.85 | 0.81 | 0.75 | 0.69 | 0.63 |
| Width of depth of field (mm) | 19.5 to 100 or larger | 5.9 to 51 | 11.5 to 23.9 | 7.9 to 12.8 | 5.8 to 8.44 | 4.49 to 6.11 |
| Angle of view(°) | 127.6 | 127.6 | 127.5 | 127.5 | 127.7 | 127.9 |
| Pitch P | 1.8 μm | | | | | |
| IH | 1.261 | | | | | |
| IH/P | 700.6 | | | | | |
| f | 1.357 | | | | | |
| IH/f | 0.929 | | | | | |
| Resolution | 33 μm (At time of 11.5 mm) | | | | | |
| $f_{focus}$ | 5.773 | | | | | |
| $f_{focus}/f$ | 4.25 | | | | | |

This embodiment has effects substantially the same as the effects in the fifth embodiment.

The focus adjusting mechanism 27 (see FIG. 2) may be configured to include a motion detecting circuit 36d as explained below.

As indicated by a dotted line in FIG. 16, the motion detecting circuit 36d functioning as motion detecting means for detecting a motion of an image between adjacent two or two or more frames from the luminance signal Y is provided in the CPU 36.

The motion detecting circuit 36d is configured by a motion detecting/comparing circuit 36e including a motion vector detecting circuit configured to detect a movement vector representing, for example, how much a feature value such as a contour detected in a set region set near a center of an image pickup region moves in the same set region in another frame adjacent to the frame and a comparing circuit configured to compare results of the detection and a threshold circuit 36f configured to generate a threshold set as a reference in performing the comparison.

The motion detecting circuit 36d compares an absolute value of the movement vector detected by the motion vector detecting circuit with the threshold of the threshold circuit 36f and, when a motion amount equal to or larger than the threshold is detected, outputs a motion detection signal to the autofocus control section 36b.

When the motion detection signal is not inputted by the motion detecting circuit 36d, the autofocus control section 36b holds a currently set focus position. When the motion detection signal is inputted, the autofocus control section 36b sets an objective optical system in a focus position different from and adjacent to the current focus position and performs autofocus control according to comparison concerning in which focus position contrast is the largest.

An operation of the autofocus control is suppressed or the suppression is released according to a temporal motion amount of an image in this way. Consequently, it is possible to more effectively perform the autofocus control.

That is, when the temporal motion amount of the image is small, an operation for repeating movement of a focus position with the autofocus is temporally suppressed. When a motion amount equal to or larger than the threshold is detected, the focus position is moved by the autofocus. Consequently, it is possible to smoothly perform the autofocus control in association with movement of an observation target due to movement of the endoscope 2. Note that the same components may be added in the endoscope apparatus 1 shown in FIG. 1.

Embodiments configured by, for example, partially combining the embodiments explained above also belong to the present invention.

What is claimed is:

1. An endoscope apparatus comprising:
an endoscope inserted into a tube cavity;
an objective optical system mounted at a distal end portion of the endoscope and configured to form an image of an object in the tube cavity, the objective optical system including a focusing lens movable in an optical axis direction and satisfying conditional expressions (1) and (2);
a solid-state image pickup device for color image pickup configured to pick up the image formed by the objective optical system, the solid-state image pickup device satisfying a conditional expression (3) below and a color separation filter being arranged for each pixel in the solid-state image pickup device;
a focus adjusting mechanism configured to move the focusing lens and automatically adjust the objective optical system to a focused state;
a moving range switching section configured to perform switching of a moving range of the focusing lens;
a moving range limiting section configured to limit the moving range using a signal in association with the switching by the moving range switching section; and
a setting information storing section configured to store information for adjusting the objective optical system to a plurality of focused states with the focus adjusting mechanism in the moving range limited by the moving range limiting section,
wherein the focusing lens includes a plurality of moving ranges not overlapping each other, each of the moving ranges including a plurality of focus positions, $$0.8 < IH/f < 1.2 \quad (1)$$

$$3.4 < f_{focus}/f < 15 \quad (2)$$

$$550 < IH/P < 1200 \quad (3)$$

where, IH represents a distance from a center in an image pickup region to a most distant position of the solid-state image pickup device, f represents a focal length of the objective optical system, $f_{focus}$ represents a focal length of the focusing lens, and P represents a pixel pitch of the solid-state image pickup device.

2. The endoscope apparatus according to claim 1, wherein, in a plurality of moving ranges limited by the moving range limiting section, as the objective optical system is set in a focused state closer to a far point side, overlapping width of depth of field of adjacent focus states is larger than on the far point side.

3. The endoscope apparatus according to claim 2, wherein the focusing lens is configured by a single lens or a cemented lens.

4. The endoscope apparatus according to claim 2, wherein change in an angle of view at a time when a focus is automatically adjusted by the focus adjusting mechanism is within 5%.

5. The endoscope apparatus according to claim 4, wherein the moving ranges are two moving ranges.

6. The endoscope apparatus according to claim 2, wherein the moving ranges are two moving ranges.

7. The endoscope apparatus according to claim 1, wherein, when the objective optical system is automatically adjusted to a focused state by the focus adjusting mechanism according to the information stored in the setting information storing section in a moving range on a farthest point side limited by the moving range limiting section, resolving power on an optical axis of the objective optical system has resolving power equal to or larger than 35 μm in a focused state in which a distance between the objective optical system and the object is equal to or smaller than 15 mm and, when a range in which MTF of a spatial frequency 1/(3×P) on the optical axis of the objective optical system is equal to or higher than 10% is defined as width of depth of field, the objective optical system has width of depth of field equal to or larger than 5 mm.

8. The endoscope apparatus according to claim 7, wherein a moving range further on a near point side than the moving range on the farthest point side is further divided into a moving range in which the width of depth of field is equal to or larger than 2.5 mm and a moving range in which the width of depth of field is smaller than 2.5 mm.

9. The endoscope apparatus according to claim 1, wherein the focus adjusting mechanism includes a motion detecting section configured to detect a motion amount in an image between temporally different frames picked up by the solid-state image pickup device, and the focus adjusting mechanism suppresses, according to whether the detected motion amount exceeds a threshold, determination concerning whether a currently-set focused state of the objective optical system is changed to another focused state.

10. An endoscope apparatus comprising:
an endoscope inserted into a tube cavity;
an objective optical system mounted at a distal end portion of the endoscope and configured to form an image of an object in the tube cavity, the objective optical system including a focusing lens movable in an optical axis direction and satisfying conditional expressions (1) and (2) below;
a monochrome solid-state image pickup device configured to pick up the image formed by the objective optical system, the solid-state image pickup device satisfying a conditional expression (3) below and generating a luminance signal for each pixel;
a focus adjusting mechanism configured to move the focusing lens and automatically adjust the objective optical system to a focused state;
a moving range switching section configured to perform switching of a moving range of the focusing lens;
a moving range limiting section configured to limit the moving range using a signal in association with the switching by the moving range switching section; and
a setting information storing section configured to store information for adjusting the objective optical system to a plurality of focused states with the focus adjusting mechanism in the moving range limited by the moving range limiting section, wherein the focusing lens includes a plurality of moving ranges not overlapping each other, each of the moving ranges including a plurality of focus positions, $$0.8 < IH/f < 1.2 \quad (1)$$

$$3.4 < f_{focus}/f < 15 \quad (2)$$

$$360 < IH/P < 800 \quad (3)$$

where, IH represents a distance from a center in an image pickup region to a most distant position of the solid-state image pickup device, f represents a focal length of the objective optical system, $f_{focus}$ represents a focal length of the focusing lens, and P represents a pixel pitch of the solid-state image pickup device.

11. The endoscope apparatus according to claim 10, wherein the moving ranges are two moving ranges.

12. The endoscope apparatus according to claim 10, wherein, when the objective optical system is automatically adjusted to a focused state by the focus adjusting mechanism according to the information stored in the setting information storing section in a moving range on a farthest point side limited by the moving range limiting section, resolving power on an optical axis of the objective optical system has resolving power equal to or larger than 35 μm in a focused state in which a distance between the objective optical system and the object is equal to or smaller than 15 mm and, when a range in which MTF of a spatial frequency 1/(2×P) on the optical axis of the objective optical system is equal to or higher than 10% is defined as width of depth of field, the objective optical system has width of depth of field equal to or larger than 5 mm.

13. The endoscope apparatus according to claim 12, wherein a moving range further on a near point side than the moving range on the farthest point side is further divided into a moving range in which the width of depth of field is equal to or larger than 2.5 mm and a moving range in which the width of depth of field is smaller than 2.5 mm.

14. The endoscope apparatus according to claim 10, wherein the focus adjusting mechanism includes a motion detecting section configured to detect a motion amount in an image between temporally different frames picked up by the solid-state image pickup device, and the focus adjusting mechanism suppresses, according to whether the detected motion amount exceeds a threshold, determination concerning whether a currently-set focused state of the objective optical system is changed to another focused state.

15. An endoscope apparatus comprising:
an endoscope inserted into a tube cavity;
an objective optical system mounted at a distal end portion of the endoscope and configured to form an image of an object in the tube cavity, the objective optical system including a focusing lens movable in an optical axis direction and satisfying conditional expressions (1) and (2);
a solid-state image pickup device for color image pickup configured to pick up the image formed by the objective optical system, the solid-state image pickup device satisfying a conditional expression (3) below and a color separation filter being arranged for each pixel in the solid-state image pickup device;
a focus adjusting mechanism configured to move the focusing lens and automatically adjust the objective optical system to a focused state;
a moving range switching section configured to perform switching of a moving range of the focusing lens;
a moving range limiting section configured to limit the moving range using a signal in association with the switching by the moving range switching section; and
a setting information storing section configured to store information for adjusting the objective optical system to a plurality of focused states with the focus adjusting mechanism in the moving range limited by the moving range limiting section,
wherein, when the objective optical system is automatically adjusted to a focused state by the focus adjusting mechanism according to the information stored in the setting information storing section in a moving range on a farthest point side limited by the moving range limiting section,
resolving power on an optical axis of the objective optical system has resolving power equal to or larger than 35 μm in a focused state in which a distance between the objective optical system and the object is equal to or smaller than 15 mm and,
when a range in which MTF of a spatial frequency 1/(3×P) on the optical axis of the objective optical system is equal to or higher than 10% is defined as width of depth of field, the objective optical system has width of depth of field equal to or larger than 5 mm, $$0.8 < IH/f < 1.2 \quad (1)$$

$$3.4 < f_{focus}/f < 15 \quad (2)$$

$$550 < IH/P < 1200 \quad (3)$$

where, IH represents a distance from a center in an image pickup region to a most distant position of the solid-state image pickup device, f represents a focal length of the objective optical system, $f_{focus}$ represents a focal length of the focusing lens, and P represents a pixel pitch of the solid-state image pickup device.

16. An endoscope apparatus comprising:
an endoscope inserted into a tube cavity;
an objective optical system mounted at a distal end portion of the endoscope and configured to form an image of an object in the tube cavity, the objective optical system including a focusing lens movable in an optical axis direction and satisfying conditional expressions (1) and (2) below;
a monochrome solid-state image pickup device configured to pick up the image formed by the objective optical system, the solid-state image pickup device satisfying a conditional expression (3) below and generating a luminance signal for each pixel;
a focus adjusting mechanism configured to move the focusing lens and automatically adjust the objective optical system to a focused state;
a moving range switching section configured to perform switching of a moving range of the focusing lens;
a moving range limiting section configured to limit the moving range using a signal in association with the switching by the moving range switching section; and
a setting information storing section configured to store information for adjusting the objective optical system to a plurality of focused states with the focus adjusting mechanism in the moving range limited by the moving range limiting section,
wherein, when the objective optical system is automatically adjusted to a focused state by the focus adjusting mechanism according to the information stored in the setting information storing section in a moving range on a farthest point side limited by the moving range limiting section, resolving power on an optical axis of the objective optical system has resolving power equal to or larger than 35 μm in a focused state in which a distance between the objective optical system and the object is equal to or smaller than 15 mm and, when a range in which MTF of a spatial frequency $1/(2 \times P)$ on the optical axis of the objective optical system is equal to or higher than 10% is defined as width of depth of field, the objective optical system has width of depth of field equal to or larger than 5 mm, $$0.8 < IH/f < 1.2 \tag{1}$$

$$3.4 < f_{focus}/f < 15 \tag{2}$$

$$360 < IH/P < 800 \tag{3}$$

where, IH represents a distance from a center in an image pickup region to a most distant position of the solid-state image pickup device, f represents a focal length of the objective optical system, $f_{focus}$ represents a focal length of the focusing lens, and P represents a pixel pitch of the solid-state image pickup device.

* * * * *